US 7,927,605 B2

(12) United States Patent
Smith

(10) Patent No.: US 7,927,605 B2
(45) Date of Patent: Apr. 19, 2011

(54) **ENVIRONMENTALLY REGULATED GENES OF *STREPTOCOCCUS SUIS***

(75) In

U.S. PATENT DOCUMENTS

2008/0241181 A1    10/2008    Smith

FOREIGN PATENT DOCUMENTS

| WO | WO 93/18164 | | 9/1993 |
|---|---|---|---|
| WO | WO 95/08732 | | 3/1995 |
| WO | WO 95/31548 | | 11/1995 |
| WO | WO 96/21485 | | 7/1996 |
| WO | WO 96/23073 | | 8/1996 |
| WO | WO 98/19689 | A | 5/1998 |
| WO | WO 00/05378 | | 2/2000 |
| WO | WO 00/05378 | | 3/2000 |
| WO | WO 02/38597 | A2 | 5/2002 |
| WO | WO 02/061070 | A2 | 8/2002 |
| WO | WO 2009/020391 | A1 | 2/2009 |

OTHER PUBLICATIONS

Jadoun, J. et al. Feb. 25, 2000. Mutation in crsR regulator reduces *Streptococcus pyogenes* internalization. Microbial Pathogen. 29: 311-317.*

Janeway-Travers. 1997. Immunobiology: The Immune System in Health and Disease. 3rd Edition.*

Smith et al. 1992. Infection and Immunity. vol. 60(6): 2361-2367.*

PCT International Search Report, PCT/NL02/00073, dated Feb. 5, 2003.

PCT International Preliminary Examination Report, PCT/NL03/00073, dated May 7, 2003.

Segers et al., Characterization of the gene encoding suflysin from *Streptococcus suis* and expression in field strains, FEMS Microbiology Letters, 1998, pp. 255-261, vol. 167.

Smith et al., Environmentally regulated genes of *Streptococcus suis*: identification by the use of iron-restricted conditions in vitro and by experimental infections of piglets, *Microbiology*, 2001, pp. 271-280, vol. 147.

Smith et al., Identification and characterization of the cps locus of *Streptococcus suis* serotype 2: the capsule protects against phagocytosis and is an important virulence factor, Infect Immun., Apr. 1999, pp. 1750-1756, vol. 67, No. 4.

Smith et al., Selection of virulence-associated determinants of *Streptococcus suis* serotype 2 by in vivo complementation, Infection and Immunity, Mar. 2001, pp. 1961-1966, vol. 69, No. 3.

Smith et al., Mutants of *Streptococcus suis* Types 1 and 2 Impaired in Expression of Muramidase-Released Protein and Extracellular Protein induce Disease in Newborn Germfree Pigs, Infection and Immunity, Oct. 1996, pp. 4409-4412, vol. 64, No. 10.

Elliott et al., Streptococcal infection in young pigs. V. An immunogenic polysaccharide from *Streptoccoccus suis* type 2 with particular reference to vaccination against streptococcal meningitis in pigs, Oct. 1980, pp. 275-285, vol. 85, No. 2.

Roberts et al., The biochemistry and genetics of capsular polysaccharide production in bacteria, Ann. Rev. Microbiol., 1996, pp. 285-315, vol. 50.

Smith et al., High efficiency transformation and gene inactivation in *Streptococcus suis* type 2, Microbiology, Jan. 1995, pp. 181-188, vol. 141.

Smith et al., Cloning and nucleotide sequence of the gene encoding the 136-kilodalton surface protein (muramidase released protein) of *Streptococcus suis* type 2, Infection and Immunity, 1992, pp. 2361-2367, vol. 60, No. 6.

Smith et al., Repeats in an extracellular protein of weakly pathogenic strains of *Streptococcus suis* type 2 are absent in pathogenic strains, Infection and Immunity, 1993, pp. 3318-3326, vol. 61, No. 8.

Smith et al., The cps locus of *Streptococcus suis* serotype 2: genetic determinant for the synthesis of sialic acid, Microbial Pathogenesis, 2000, pp. 127-134, vol. 29, No. 2.

Watson et al., Pneumococcal Virulence Factors and Host Immune Responses to Them, European Journal of Clinical Microbiology & Infectious Diseases, Jun. 1995, pp. 479-490, vol. 14, No. 6.

Joh et al., Role of fibronectin-binding MSCRAMMs in bacterial adherence and entry into mammalian cells, Matrix Biology, 1999, pp. 211-223, vol. 18.

UniProtKB/TrEMBL entry Q8RP86 (visited Feb. 18, 2009), <http://ww.expasy.org/uniprot/Q8RP86_STRSU>.

EMBL Nucleotide Sequence Entry EMBLCDS:AAL85276 (visited Feb. 18, 2009). <http://srs.ebi.ac.uk.srsbin/cgi-bin/wgetz?-e+[EMBLCDS:AAL85276]+-NEWiD>.

Uniprot Q8RP86 (visited Feb. 18, 2009), <http://www.uniprot.org/uniref/?query=Q8RP86+AND+identity%3A0.5>.

U.S. Appl. No. 11/982,192, filed Oct. 31, 2007, Smith, Environmentally Regulated Genes of *Streptococcus suis*.

Dutch Text Annual Report ID-DLO *Streptococcus suis*, 1996, with English translation of said report.

Office Action for U.S. Appl. No. 11/516,691, dated Oct. 15, 2007.
Office Action for U.S. Appl. No. 11/516,691, dated Feb. 26, 2008.
Office Action for U.S. Appl. No. 11/516,691, dated Apr. 22, 2008.
Office Action for U.S. Appl. No. 11/516,691, dated Dec. 5, 2008.
Office Action for U.S. Appl. No. 11/516,691, dated Jun. 22, 2009.
Office Action for U.S. Appl. No. 11/516,691, dated Nov. 25, 2009.
Notice of Allowance for U.S. Appl. No. 11/516,691, dated Mar. 19, 2010.
Office Action for U.S. Appl. No. 11/982,192, dated May 17, 2010.

Allgaier et al., Relatedness of *Streptococcus suis* isolates of various serotypes and clinical backgrounds as evaluated by macrorestriction analysis and expression of potential virulence traits. Journal of Clinical Microbiology, 2001, pp. 445-453, vol. 39, No. 2.

Busque et al., Immunization of pigs against *Streptococcus suis* serotype 2 infection using a live avirulent strain, Can J Vet Res., Oct. 1997, pp. 275-279, vol. 61, No. 4.

Charland et al., *Streptococcus suis* serotype 2 mutants deficient in capsular expression, Microbiology, Feb. 1991, pp. 325-332, vol. 144, No. 2.

Database EMBL, 'Online' MeNab, *S. gordonii* partial aldB gene, cabA gene & fbpA gene, Database accession No. X65164, XP002213089, Sep. 2001.

De Greeff et al., Distribution of Environmentally Regulated Genes of *Streptococcus suis* Serotype 2 among 5, suis Serotypes and Other Organisms, Journal of Clinical Microbiology, Sep. 2002, pp. 3261-3268, vol. 40, No. 9.

Elliott et al., Streptococcal infection in young pigs. V. An immunogenic polysaccharide from *Streptococcus suis* type 2 with particular reference to vaccination against streptococcal meningitis in pigs, Oct. 1980, pp. 275-285, vol. 85, No. 2.

Kawabata et al., Molecular cloning, sequence and characterization of a novel streptococcal phesphoglycerate dehydrogenase gene, Oral Microbiology and Immunology, 2000, pp. 58-62, vol. 15.

Kolkman et al., Diversity of capsular polysaccharide synthesis gene clusters in *Streptococcus pneumoniae*, J. Biochem., May 1998, pp. 937-943, vol. 123, No. 5.

Koskiniemi et al., Identification of two genes, cpsX and cpsY, with putative regulatory function on capsule expression in group B streptococci, FEMS Immunology and Medical Microbiology, 1998, pp. 159-168, vol. 21.

McNab, Cloning and sequence analysis of thyridine kinase from the oral bacterium *Streptococcus gordonii*, FEMS Microbiology Letters, 1996, pp. 103-110, vol. 135.

Munoz et al., Characterization of ISI515, a Functional Insertion Sequence in *Streptococcus pneumoniae*, Journal of Bacteriology, Mar. 1998, pp. 1381-1388, vol. 180, No. 6.

Quessy et al., Immunization of mice against *Streptococcus suis* serotype 2 infections using a live avirulent strain, Can J. Vet Res., Oct. 1994, pp. 229-301, vol. 58, No. 4.

Baums et al., Clinical and Vaccine Immunology, Feb. 2009, pp. 200-208, vol. 16, No. 2.

Chothia et al., The EMBO Journal, 1986, pp. 823-826, vol. 5, No. 4.

Database EMBL 'Online' McNab, *S. gordonii* partial aldB gene, csbA gene & fbpA gene, Database accession No. X65164, XP002213089, Sep. 2001.

Devriese et al., Avian Pathology, 1994, pp. 721-724, vol. 23.

Greenspan et al., Nature Biotechnology, 1999, pp. 936-937, vol. 7.

Hampson et al., *Journal of Clinical Microbiology*, 1993, pp. 2895-2900, vol. 31, No. 11.

Merck Manual On-line Streptococcal Disease (pp. 1-6), retrieved from web on Nov. 16, 2009.

Merriam-Webster Online Dictionary, (visited Jun. 7, 2004) <http://www.m-w.com/cgi-bin/dictionary?book-Dictionary&va=vaccine&x=19&y=12>.

Mikayama et al., Nov. 1993. Proc. Natl. Acad. Sci., USA., pp. 10056-10060, vol. 90.

PCT International Preliminary Examination Report, PCT/NL99/00460, dated Oct. 27, 2000.

PCT International Search Report, PCT/NL99/00460, dated Apr. 5, 2000, 6 pages.

Rudinger et al., Characteristics of the amino acids as components of a peptide hormone sequence, Peptide hormones. Biol. Council, Jun. 1976, pp. 1-7.

Smith et al., submitted Sep. 10, 2000, Genbank Accession No. AF306940.

Wisselink et al., Assessment of protective efficacy of live and killed vaccines based on a non-encapsulated mutant of *Streptococcus suis* serotype 2. Veterinary Microbiology, 2002, pp. 155-168, vol. 84.

Zhang et al., Identification and characterization of an antigen VII family protein produced by group A *Streptococcus*, Infection and Immunity, Jul. 2006, pp. 4200-4213, vol. 74, No. 7.

Mikayama et al., Nov. 1993, Proc. Natl. Acad. Sci., USA., pp. 10056-10060, vol. 90.

Litwin et al., Role of Iron Regulation in Virulence Genes, Clinical Microbiology Reviews, Apr. 1993, pp. 137-140, vol. 6, No. 2.

Courtney et al., Cloning, Sequencing, and Expression of a Fibronectin/Fibrinogen-Binding Protein from Group A *Streptococci*, Infection and Immunity, Sep. 1994, pp. 3937-3946, vol. 62, No. 9.

Database EMBL [Online] *Streptococcus pneumoniae* adherence and virulence protein A (pavA) gene, complete cds, Nov. 4, 1999, XP002332859, retrieved from EBI accession No. EM_PRO:AF181976, Database accession No. AF181976.

Holmes et al., The pavA gene of *Streptococcus pneumoniae* encodes a fibronectin-binding protein that is essential for virulence, Molecular Microbiology, 2001, pp. 1395-1408, vol. 41, No. 6.

Database EMBL [Online], *S. gordonii* partial aldB gene, cshA gene & fbpA gene, XP002332860 retrieved from EBI accession No. EM_PRO:SGSCHAG, Database accession No. X65164.

Christie et al., Expression of fibronectin-binding protein FbpA modulates adhesion in *Streptococcus gordonii*, Microbiology, 2002, pp. 1615-25, vol. 148.

European Search Report, EP 02 71 1531 dated Jun. 22, 2005.

Ellis, R.W. (Chapter 29 of "Vaccines" Plotkin, S.A. et al. (eds) published by W. B. Saunders company (philadelphia) in 1988, especially p. 571.

Herbert et al eds, The Dictionary of Immunology, Academic Press, 1995.

Gottschalk et al., Journal of Clinical Microbiology, Dec. 1999, pp. 4242, vol. 37, No. 12.

Segura et al., FEMS Immunology and Medical Microbiology, 1998, pp. 189-195, vol. 12.

Reams et al., J. Vet. Diagn. Invest, 1996, pp. 119-121, vol. 8.

Staats et al., Veterinary Research Communications, 1997, pp. 381-407, vol. 21.

Brazeau et al., Microbiology, 1996, pp. 119-121, vol. 8.

\* cited by examiner

ENVIRONMENTALLY REGULATED GENES OF *STREPTOCOCCUS SUIS*

CROSS-REFERENCE TO RELATED APPLICATIONS

This application is a continuation of PCT/NL02/00073, filed Jan. 31, 2002, designating the United States of America, corresponding to PCT International Publication WO 02/061070 (published in English on Aug. 8, 2002), the contents of which are incorporated herein in its entirety.

TECHNICAL FIELD

The invention relates to the field of the diagnosis of and vaccination against Streptococcal infections, and to the detection of virulence markers of Streptococci.

BACKGROUND

*Streptococcus* species, of which there are a large variety of that cause infections in domestic animals and man, are often grouped according to Lancefield's groups. Typing according to Lancefield occurs on the basis of serological determinants or antigens that are, among others, present in the capsule of the bacterium and only allows for an approximate determination. Often, bacteria from a different group show cross-reactivity with each other, while other Streptococci cannot be assigned a group-determinant at all. Within groups, further differentiation is often possible on the basis of serotyping. These serotypes further contribute to the large antigenic variability of Streptococci, a fact that creates an array of difficulties within diagnosis of and vaccination against Streptococcal infections.

Lancefield group A *Streptococcus* (GAS, *Streptococcus pyogenes*) are common with children and cause nasopharyngeal infections and complications thereof. Animals, such as cattle, are susceptible to GAS, wherein mastitis is often found associated with the cattle.

Lancefield group B *Streptococcus* (GBS) are most often seen with cattle and cause mastitis. However, human infants are susceptible as well, often with fatal consequences. Group B Streptococci (GBS) constitute a major cause of bacterial sepsis and meningitis among human neonates born in the United States and Western Europe and are emerging as significant neonatal pathogens in developing countries.

Lancefield group C infections, such as those with *S. equi, S. zooepidemicus, S. dysgalactiae*, and others are mainly seen associated with horses, cattle and pigs, but can also cross the species barrier to humans.

Lancefield group D (*S. bovis*) infections are found with all mammals and some birds, sometimes resulting in endocarditis or septicemia.

Lancefield groups E, G, L, P, U and V (*S. porcinus, S. canis, S. dysgalactiae*) are found with various hosts and cause neonatal infections, nasopharyngeal infections or mastitis.

Within Lancefield groups R, S, and T (and with ungrouped types), *S. suis* is found and is an important cause of meningitis, septicemia, arthritis and sudden death in young pigs. Incidentally, *S. suis* can also cause meningitis in man.

Ungrouped *Streptococcus* species, such as *S. mutans*, causes carries with humans. *S. uberis* causes mastitis with cattle, *S. pneumonia* causes major infections in humans, and *Enterococcus faecilalis* and *E. faecium* further contribute to the large group of Streptococci. *Streptococcus pneumoniae* (the pneumococcus) is a human pathogen causing invasive diseases, such as pneumonia, bacteremia, and meningitis.

Little is known about the pathogenesis of the disease caused by Streptococci. Various cellular components, such as muramidase-released protein (MRP), extracellular factor (EF) and cell-membrane-associated proteins including fimbriae, hemagglutinins, and hemolysin have been suggested as virulence factors. However, the precise role of these protein components in the pathogenesis of the disease remains unclear. It is known and generally accepted that the polysaccharidic capsule of various Streptococci and other gram-positive bacteria play an important role in pathogenesis. The capsule enables these microorganisms to resist phagocytosis and is, therefore, regarded as an important virulence factor or marker.

In particular, *Streptococcus suis* is an important cause of meningitis, septicemia, arthritis and sudden death in young pigs. It can also cause meningitis in man. Attempts to control the disease are hampered by the lack of sufficient knowledge about the pathogenesis of the disease and the lack of effective vaccines and sensitive diagnostic methods.

So far, 35 serotypes of *S. suis* are described. Virulence of *S. suis* can differ within and among serotypes. Worldwide, *S. suis* serotype 2 is the most frequently isolated serotype. Within *S. suis* serotype 2, pathogenic, weak-pathogenic and non-pathogenic strains can be found. The pathogenic strains cause severe clinical signs of disease in pigs and large numbers of bacteria can be re-isolated from the central nervous system (CNS) and the joints after experimental infection. The weak-pathogenic strains cause only mild clinical signs of disease and infrequently are bacteria re-isolated from the CNS and the joints after experimental infection. The non-pathogenic strains are completely avirulent in young pigs after experimental infection.

The 136-kDa muramidase-related protein (MRP) and the 110-kDa extracellular factor (EF) are generally considered as important virulence markers for *S. suis* serotype 2 strains isolated in Europe and the United States. However, differences in virulence between pathogenic, weak-pathogenic and non-pathogenic strains cannot exclusively be explained by differences in their MRP and EF expression patterns. In addition, it is known that the capsule of *Streptococcus suis* serotype 2 is an important virulence factor. However, since pathogenic, weak-pathogenic and non-pathogenic strains seem to be fully encapsulated after growth in vitro and in vivo, it is not likely that the level of encapsulation of these fully encapsulated strains is associated with their difference in virulence.

SUMMARY OF THE INVENTION

The invention discloses a method for modulating virulence of a *Streptococcus* comprising modifying a genomic fragment of *Streptococcus*. The genomic fragment comprises at least a functional part of a fragment identifiable by hybridization in *Streptococcus suis* to a nucleic acid or fragment thereof as shown in SEQ ID NOS: 8 through 45 and obtaining a clone including the modified genomic fragment. In one exemplary embodiment, the genomic fragment comprises at least a functional part of a gene, the expression of which can be environmentally regulated in *S. suis* by iron-restricted conditions. In another exemplary embodiment, the genomic fragment comprises at least a functional part of a gene which is expressed in a wild-type *S. suis* infected pig (in vivo). In a further exemplary embodiment, selection under iron-restricted conditions is combined with selection in vivo. In one embodiment, the gene encodes a fibronectin/fibrinogen-binding protein. The method disclosed herein is useful for modulating virulence of *Streptococcus suis* and comprises functionally deleting the expression of at least the functional part of the gene by *Streptococcus*.

The phrase "functionally deleting" as used herein refers to any technique known in the art (such as allowing for a deletion, insertion, mutation or the occurrence of a frame-shift in the open-reading frame of the respective gene) that is instrumental in hampering or inhibiting the expression of a gene-product (be it mRNA and/or protein) of the gene. Thus, the invention discloses a clone of a *Streptococcus* obtained or obtainable by a method according to the invention.

To get insight in the differences between pathogenic, weak-pathogenic and non-pathogenic strains or clones that are determined by their difference in virulence, the invention describes the identification of environmentally regulated genes of *Streptococcus suis* by iron-restricted conditions and by experimental infection of piglets. Eighteen unique iron-restricted induced (iri) genes and 22 unique in vivo selected (ivs) genes of *S. suis* were found. None of the ivs genes was exclusively expressed in vivo. Four iri genes were substantially identical to four ivs genes selected in piglets. Two ivs genes were similar to genes for putative virulence factors. One of these ivs genes was substantially identical to the epf gene of virulent *S. suis* serotype 2 strains and the other ivs gene showed homology to a gene encoding a fibronectin-binding protein of *Streptococcus gordonii*.

In yet another embodiment, the invention discloses a study of the characteristics of fibronectin- and fibrinogen-binding protein of *Streptococcus suis* (FBPS) and its gene as identified herein. The ability to bind fibronectin, either in fluid phase or immobilized onto a surface, is a property of *S. suis* and is one of the mechanisms *S. suis* uses for attachment to and invasion of host cells. Therefore, FBPS is an important virulence factor. The gene encoding FBPS was identified using an in vivo selection system in pigs as described herein, thus, showing an important role of the protein in vivo. This finding was supported by the observation that isogenic FBPS mutants, herein also disclosed, of *S. suis* are attenuated in pigs. Surprisingly, FBPS bound to fibronectin, as well as to fibrinogen, but did not show the structural characteristics of the fibronectin-binding proteins most commonly described and explains why FBPS has not been found earlier. Most fibronectin-binding proteins described to date are large cell surface proteins with predicted sizes of 60-100 kDa and have similar structural organizations. The proteins contain an N-terminal signal sequence as well as the cell wall signaling sequence (LPXTGE) (SEQ ID NO: 1). The Fn-binding sites include 30-42 amino acid long motifs, repeated 3-4 times. In particular, the first fibronectin- and fibrinogen-binding protein of *S. suis* is disclosed herein. The gene encoding FBPS was cloned and sequenced and FBPS was purified. Binding of FBPS to human fn and fgn was shown. FBPS was shown to be involved in the colonization of the organs specific for an *S. suis* infection in piglets, but not in the colonization of *S. suis* on the tonsils of piglets.

Many Streptococci and Staphylococci have several different fibronectin- and/or fibrinogen-binding proteins, most of which are very large, about 130 kDa. Until now, *S. pyogenes* was the only organism to have a large, as well as a smaller (54 kDa), FnBP. The existence of more than one FnBP explains why in some organisms, isogenic mutants defective in only one of the FnBPs can still bind to fn and/or fgn can be further attenuated in vivo in relation to fibronectin binding.

The role of FBPS in the pathogenesis of *S. suis* was studied in an experimental infection model in piglets. Since we were unable to determine a $LD_{50}$ values for the mutant clones because no lethal dose could be established using normally used numbers of bacteria, it was decided to compare the virulence of the isogenic FBPS clone to the wild-type *S. suis* in a competitive infection assay in piglets. This kind of co-colonization experiment has been successfully applied to determine the virulence of mutants of *Actinobacillus pleuropneumoniae* in piglets. The data showed that the mutant clone was capable of colonizing the tonsil as efficiently as the wild-type. This strongly indicates that FBPS is not involved in the colonization of the tonsil. The data also indicated that FBPS does play a role in the colonization of specific organs, since in the competition assay, joints and the CNS were more efficiently colonized by wild-type than by mutant bacteria.

In addition, higher numbers of wild-type bacteria were re-isolated from the specific organs compared to the numbers of mutant bacteria, indicating that the mutant clone is attenuated in vivo. Although the number of pigs used for this experiment was low, the data indicates that the FBPS mutant is less virulent than the wild-type strain. It was demonstrated that FBPS reacted with a convalescent serum of a pig that survived an *S. suis* infection. Therefore, FBPS is immunogenic in pigs and this finding demonstrates that FBPS of *S. suis* is expressed under in vivo conditions.

It is also shown that the fbps gene was present in all known serotypes of *S. suis* (except for two), as well as in all three phenotypes of serotype 2. This suggests that the fbps gene is present among most serotypes. However, the expression of FBPS in all serotypes and phenotypes was not studied. Therefore, it is possible that although all strains, except for serotypes 32 and 34, possess the fbps gene, not all strains express FBPS. Based on the facts that FBPS is immunogenic in pigs and that the fbps gene is present in all prevailing *S. suis* serotypes, (except for two), FBPS is an attractive candidate for a cross-protective vaccine against essentially all serotypes. In one embodiment, the mutant strain 10ΔFBPS may be used in the vaccine, which mutant is possibly further attenuated by deleting one or more virulence factors as described herein. In another embodiment, this vaccine is based on purified FBPS protein or an antigenic part thereof with a suitable adjuvant.

To further validate a method for identifying a virulence factor, the role of the fibronectin-/fibrinogen-binding protein (FBPS) in the pathogenesis of *S. suis* serotype 2 was investigated in piglets as described herein. The complete gene encoding FBPS from *S. suis* serotype 2 was cloned in *E. coli* and sequenced. The occurrence of the gene in various serotypes was analyzed by hybridization studies. The FBPS protein was expressed in *E. coli*, purified and binding to human fibronectin and fibrinogen was demonstrated. The induction of antibodies in piglets was studied upon infection. An isogenic mutant unable to produce FBPS was constructed and the virulence of the wild-type and mutant strains was compared in a competitive infection model in young piglets. Organ cultures showed that FBPS was not required for colonization of the tonsils, but that FBPS played a role in the colonization of the specific organs involved in an *S. suis* infection. Therefore, the FBPS mutant was considered as an attenuated mutant which is useful in a vaccine. Alternatively, a vaccine is used that mainly includes the FBPS protein or at least of an antigenic part thereof, such that an FBPS-specific antibody or T-cell response in pigs is developed after vaccination with the FBPS or antigenic part thereof.

Two additional ivs genes showed homology to environmentally regulated genes previously identified by using an in vivo expression technology (IVET) selection in other bacterial species. One of these showed similarity to the agrA gene of *Staphylococcus aureus*, a key locus involved in the regulation of numerous virulence proteins.

Thus, the invention also discloses a method for assaying virulence of a Streptococcus comprising assaying a genomic fragment of Streptococcus, wherein the genomic fragment comprises at least a functional part of a fragment identifiable by hybridization in Streptococcus suis to a nucleic acid or fragment thereof as described herein.

The invention also discloses a vector comprising a nucleic acid according to the invention and a host cell comprising a nucleic acid or a vector according to the invention. Such a host cell comprises an easily modifiable organism such as E. coli. However, other host cells, such as a recombinant Streptococcus comprising a vector. or nucleic acid according to the invention are also disclosed herein.

The invention additionally discloses a vaccine comprising a nucleic acid, a vector or a host cell according to the invention, and use of such a vaccine in the prevention and/or treatment of Streptococcal infections.

Also disclosed is a protein or fragment thereof encoded by a nucleic acid according to the invention, such as a protein encoded by a nucleic acid or fragment thereof disclosed herein or functional, i.e., antigenic fragment thereof. The invention also discloses an antibody directed against a protein or fragment thereof according to the invention and an antigen reactive with such an antibody, for example comprising a protein or fragment. Such a protein or fragment thereof need not be obtained by recombinant means. Synthesis of peptides, according to their amino acid sequence, is as well equally possible. Such antigens and antibodies as described herein can be used in a diagnostic test comprising an antibody according to the invention, or within a vaccine or diagnostic test comprising an antigen according to the invention. Such vaccines and diagnostic tests can be used in the field of the diagnosis of and vaccination against Streptococcal infections and for the detection of virulence markers of Streptococci.

DETAILED DESCRIPTION

Figure 1:
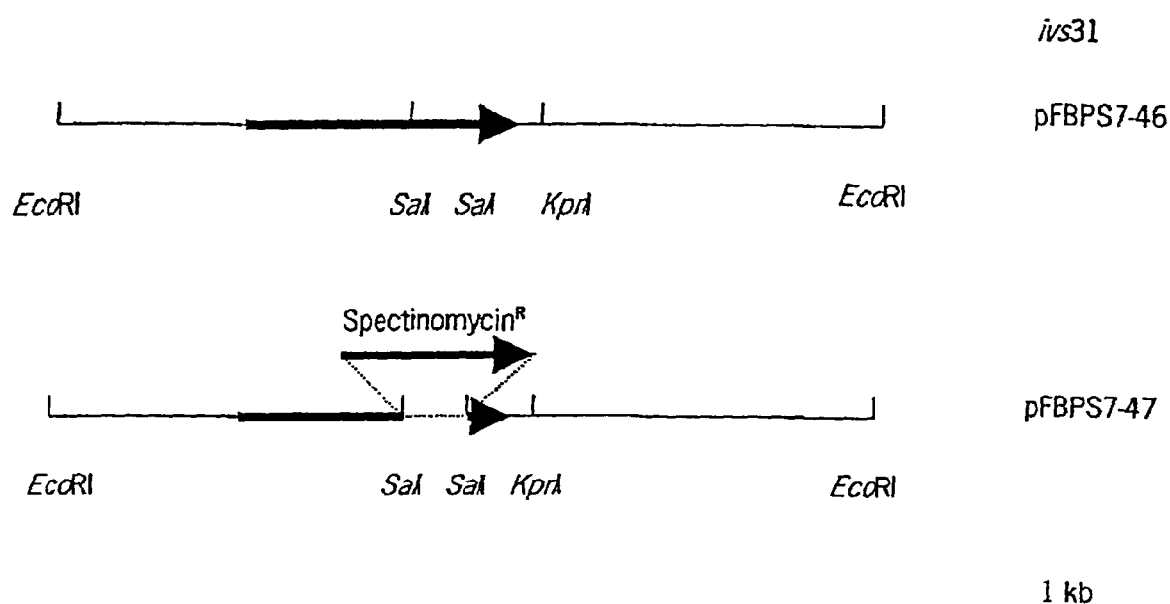
FIG. 1 is a schematic presentation of the procedure used to clone the fbps gene of S. suis serotype 2 and the construction of an insertional knock-out mutant in S. suis serotype 2. A 5 kb EcoRI fragment was cloned in pGEM7Zf(+), yielding pFBPS7-46. In pFBPS7-47, the 382 bp SalI-SalI fragment of pFBPS7-46 was replaced by 1.2 kb spectinomycin-resistance gene, after the vector was made blunt to obtain an insertional knock-out of fbps. Ivs-31: in vivo selected gene 31.

Streptococcus suis is an important cause of meningitis, septicemia, arthritis and sudden death in young pigs (Clifton-Haclley, 1983; Vecht et al., 1985). It can also cause meningitis in man (Arends and Zanen, 1988). Attempts to control the disease are still hampered by the lack of sufficient knowledge about the pathogenesis of the disease, the lack of effective vaccines and sensitive diagnostic methods. To meet these shortages, it is necessary to identify the genes that are involved in the pathogenic process. So far, only a limited number of S. suis genes are known (Smith et al., 1992; Smith et al., 1993; Serhir et al., 1997; Segers et al., 1998; Smith et al., 1999; and accession nos. AF106927, Z95920 and A57222) and of these, only a few are putatively involved in virulence (Smith et al., 1992; Smith et al., 1993; Jacobs et al., 1994; Gottschalk et al., 1995; Segers et al., 1998; Smith et al., 1999). Previously, putative virulence factors have been identified after growth of the bacteria in standard laboratory media. However, it is known that many important virulence factors are environmentally regulated and are induced at specific stages of the infection process (Mahan et al., 1993).

Recently, several approaches have been reported that allow the identification of genes that are specifically expressed in the host. Examples are signature-tagged mutagenesis (STM) and in vivo expression technology (IVET; Mahan et al., 1993; Carnilli and Mekalanos, 1995; Hensel et al., 1995; Mahan et al., 1995; Mei et al., 1997; Young and Miller, 1997; Chiang and Mekalanos, 1998; Coulter et al., 1998; Lowe et al., 1998; Polissi et al., 1998; Camacho et al., 1999; Darwin et al., 1999; Edeistein et al., 1999; Fuller et al., 1999; Zhao et al., 1999). In addition, important virulence proteins could also be identified by the selection of genes specifically expressed under conditions mimicking in vivo conditions, for example by growth in iron-restricted conditions (Litwin and Calderwood, 1993; Martinez et al., 1990).

The present invention identifies virulence genes of S. suis by selecting environmentally regulated genes by experimental infections of piglets and by the use of iron-restricted conditions in vitro. For this purpose, chromosomal DNA fragments of S. suis were cloned in a plasmid in front of a promoterless erythromycin-resistance gene. Subsequently, the library was used for the selection of bacteria in which erythromycin resistance was induced under iron-restricted conditions. In addition, erythromycin-resistant bacteria were selected after infection of piglets with the library and treatment of the piglets with erythromycin. Pigs were used instead of mice for these experiments since it was recently shown that virulence of S. suis is different in these two animal species (Vecht et al., 1997). Using this approach, 18 unique iron-restriction-induced (iri) genes, as well as 22 unique in vivo selected (ivs) genes, were identified, several of which are putatively involved in virulence (Smith et al., 1993; Smith et al., 1996).

Methods.

Bacterial strains and growth conditions. The bacterial strains and plasmids used in this study are listed in Table 1. *S. suis* strains were grown in Todd-Hewitt broth (Oxoid), and plated on Columbia agar (Oxoid) containing 6% (v/v) horse blood. For the selection of genes induced in iron-limited conditions, *S. suis* cells. were plated on agar plates containing Todd-Hewitt medium, 5% (w/v) yeast extract and 75 µM deferoxamine mesylate (Sigma). Control plates were supplemented with 38 µM $FeSO_4.7H_2O$ (Sigma). If required, antibiotics were added at the following concentrations: 100 µg spectinomycin $ml^{-1}$ and 1 µg erythromycin $ml^{-1}$. *E. coli* strains were grown in Luria broth (Miller, 1972) and plated on Luria broth containing 1.5% (w/v) agar. If required, 50 µg ampicillin $ml^{-1}$ or 50 µg spectinomycin $ml^{-1}$ was added.

Construction of pIVS-E. The IVS selection vector used in this study comprises a spectinomycin-resistance gene, a promoterless erythromycin-resistance gene and the origin of replication of the plasmid pWVO1 (Van der Vossen et al., 1987). To construct this pIVS-E, the spectinomycin-resistance gene was amplified from pKUN19-spc (Konings et al., 1987; Smith et al., 1995). In a PCR reaction, the primers 5'-TGCAT-GCATGGATCCATCGA TTTTCGTTCG-3' (SEQ ID NO: 2) and 5'-CGAGCTCGGTACCTGATTACCAATTAGAAT-3' (SEQ ID NO: 3), which contained NsiI and SacI restriction sites at their respective 5'-ends were used. The obtained PCR product was digested with NsiI and SacI and ligated into pGKV210 (Van der Vossen et al., 1987) that had been digested with SacI (partially) and NsiI. The resulting plasmid was designated pGKV210-spc. pE194 (Horinouchi and Weisblum, 1982) was used as a template for the amplification of a promoterless erythromycin-resistance gene. To do this, the primers 5'-GGGTCGACCCTATAACCAAATTAAA-GAGGG-3' (SEQ ID NO: 4) and 5'-CCCAAGCT-TGGGCAGTTTATGCATCCCTTAAC-3' (SEQ ID NO: 5) were used in a PCR reaction. These primers contained SalI and HindIII restriction sites at their respective 5'-ends. The amplified fragment was digested with SalI and HindIII and the fragment was ligated into pGKV210-spc that had been digested with SalI and HindIII. The resulting plasmid was designated pIVS-E. To construct pIVS-PE, the promoter region of the mrp gene was inserted into pIVS-E 5' to the promoterless erythromycin-resistance gene. The promoter region of the mrp gene was amplified by PCR from pMRP11 (Smith et al., 1992) using the primers 5'-CCCAAGCTTGG-GAATTCATAATGTTTTTTTGAGG-3' (SEQ ID NO: 6) and 5'-GCGTCGACATCTACGCATAAAAAATCCCCC-3' (SEQ ID NO: 7). These primers contained EcoRI and SalI sites at their respective 5'-ends. Amplified DNA was digested with EcoRI and SalI and the resulting fragment was ligated into EcoRI and SalI-digested pIVS-E.

Construction of Genomic *S. suis* Libraries in pIVS-E. Alu I partial digests of *S. suis* serotype 2 strain 10 DNA were size fractionated (500-1000 bp) on a 0.8% (w/v) agarose gel. The purified fragments were ligated to SmaI and calf intestinal phosphatase digested pIVS-E and the ligation mixtures were transformed to *E. coli* XL2-blue cells. Spectinomycin-resistant colonies were selected. Analysis of the transformants by PCR showed that more then 80% contained an insert. From 15 pools of about 2000-3000 independent *E. coli* transformants, plasmid DNA was isolated. This plasmid DNA was subsequently used for the electrotransformation of *S. suis* strain 10 (Smith et al., 1995). This resulted in approximately 30,000 independent *S. suis* transformants. The transformants were pooled and stored at −80° C.

DNA Techniques. Routine DNA manipulations and PCR reactions were performed as described by Sambrook et al. (1989). DNA sequences were determined on a 373A DNA Sequencing System (Applied Biosystems). Samples were prepared by using the ABI/PRISM dye terminator cycle sequencing ready reaction kit (Applied Biosystems). Custom-made sequencing primers were purchased from Life Technologies. Sequencing data were assembled and analyzed using the McMollyTetra software package. The BLAST program was used to search for protein sequences similar to the deduced amino acid sequences.

PCR reaction mixtures (50 µl) contained 10 mM Tris-HCl, pH 8.3, 1.5 mM $MgCl_2$, 50 mM KCl, 0.2 mM of each of the four deoxynucleotide triphosphates, 1 µM of each of the primers and 1 U of AmpliTaq Gold DNA polymerase (Perkin Elmer Applied Biosystems). DNA amplification was carried out in a Perkin Elmer 9600 thermal cycler and the program included an incubation for ten minutes at 95° C. and 30 cycles of one minute at 95° C., two minutes at 56° C. and two minutes at 72° C.

Assessment of Erythromycin Levels in Treated Piglets. One-week-old specific pathogen-free (SPF) piglets were treated orally with erythromycin stearate (Abbott, 20 or 40 mg body weight $kg^{-1}$) or intramuscularly with erythromycin (Erythrocin 200; Sanofi Santé, 20 or 40 mg body weight $kg^{-1}$). Blood samples were collected 3 hours, 6 hours or 24 hours after the administration of the antibiotics to determine erythromycin levels.

Experimental Infections. Gnotobiotic Great Yorkshire and Dutch Landrace crossed piglets were obtained from sows by cesarian section. The surgery was performed in sterile flexible film isolators. The piglets were allotted to groups, each having 4 piglets, and were housed in sterile stainless steel incubators. Housing conditions and feeding regimens were as described (Vecht et al., 1989; Vecht et al., 1992). One-week-old piglets were inoculated intravenously with *S. suis* strain 10 (pIVS-E), 10 (pIVS-PE) or 10 (pIVS-RE) as described (Vecht et al., 1989; Vecht et al., 1992, Table 3). Two hours after infection, the pigs were injected intramuscularly with erythromycin for the first time and thereafter received erythromycin twice a day: once intramuscularly (Erythrocin, 40 mg body weight $kg^{-1}$) and once orally (erythromycin stearate, 40 mg body weight $kg^{-1}$).

Piglets were monitored twice a day for clinical signs of disease, such as fever, nervous signs and lameness. Blood samples were collected three times a week from each pig. Leukocyte concentrations were determined using a conducting counter (Contraves A. G., Switzerland). To monitor infection with *S. suis* and to check for absence of contaminants, swabs of the nasopharynx and of feces were collected daily. The swabs were directly plated onto Columbia agar containing 6% (v/v) horse blood. After the piglets were killed, they were examined for gross pathological changes. Tissue specimens were collected from the central nervous system, serosae, joints, lungs, heart and tonsils. The tissues were homogenized in the presence of Todd-Hewitt medium using an Ultra-Turrax tissuemizer (Omni International) and frozen at −80° C. in the presence of 15% (v/v) glycerol.

Results.

Promoter Selection System.

The plasmid pIVS-E was constructed to allow introduction of *S. suis* DNA fragments into a number of unique restriction sites in front of a promoterless erythromycin-resistance resistance gene. The plasmid carries the origin of replication of pWVO1, which functions in *E. coli* and in *S. suis* (Smith et al., 1995). *S. suis* strain 10 cells containing pIVS-E were sensitive to 1 µg erythromycin ml$^{-1}$ on agar plates. In pIVS-PE the promoter of the mrp gene of *S. suis* (Smith et al., 1992), which is highly expressed in vivo as well as in vitro, drives expression of the erythromycin-resistance gene. *S. suis* strain 10 cells containing pIVS-PE were resistant to high concentrations of erythromycin (>256 µg erythromycin ml$^{-1}$) on agar plates. A *S. suis* DNA library in pIVS-E (pIVS-RE) was constructed and 30,000 individual *S. suis* clones or mutants were obtained. As determined by analysis of 24 randomly selected transformants, more than 80% of these clones or mutants contained an insert (results not shown). Moreover, 2% of the clones were resistant to 1 µg erythromycin ml$^{-1}$ on agar plates indicating the presence of some promoter sequences that were functional in vitro.

Selection of Promoters Induced Under Iron-Restricted Conditions.

Gene sequences that were specifically induced on agar plates under iron-restricted conditions were selected. For this purpose, about 96,000 c.f.u. were plated under iron-limiting conditions on agar plates containing deferoxamine mesylate and erythromycin. The 1500 colonies that grew on these plates were inoculated onto plates containing erythromycin, deferoxamine mesylate and FeSO$_4$. Twenty-four clones showed reduced growth in the presence of FeSO$_4$. The inserts of the 24 selected iri clones were amplified by PCR using primers complementary to the 5' ends of the erythromycin- and spectinomycin-resistance genes and the nucleotide sequences of these fragments were determined. The sequence data showed that the 24 clones contained 18 unique sequences. The 18 sequences were analyzed for similarity to known genes by comparison with the sequences in the GenBank/EMBL and SWISSPROT databases. One sequence, iri31, was identical to cps2A, a previously identified *S. suis* gene putatively involved in the regulation of capsule expression (Smith et al., 1999). Fourteen iri sequences were similar to sequences of known, non-*S. suis*, genes. Three of these sequences (iri2 (SEQ ID NO: 15), iri1, 6 and 22 (SEQ ID NO: 8), and iri34 (SEQ ID NO: 21) were similar to sequences of environmentally regulated genes previously selected by applying the IVET to *V. cholerae* (Camilli and Mekalanos, 1995), *S. aureus* (Lowe et al., 1998) and *P. aeruginosa* (Wang et al., 1996), respectively. One, contained in iri1, 6, and 22 (SEQ ID NO: 8), was similar to the agrA gene of *Staphylococcus aureus*, a key locus involved in the regulation of numerous virulence proteins. Three iri sequences had no significant similarity to any sequences in the databases (Table 2).

Conditions for Selection of Promoter Sequences in Piglets.

To determine the antibiotic treatment regime required for a successful selection of in vivo-expressed promoter sequences, piglets were treated with different concentrations of erythromycin once a day. The erythromycin was administered either orally or intramuscularly. Levels of erythromycin in sera were determined 3, 6 or 24 hours after treatment over one week. High erythromycin levels were detected three hours and six hours after both treatments (results not shown). However, 24 hours after the treatments, the levels decreased dramatically. Based on these data, we hypothesized that for efficient promoter selection, it was necessary to treat the animals twice a day with erythromycin (40 mg kg$^{-1}$), once intramuscularly (at 9 a.m.) and once orally (at 4 p.m.).

To test this hypothesis, pigs were inoculated either with *S. suis* strain 10 (pIVS-PE) or with strain 10 (pIVS-E). In pIVS-PE, the promoter of the mrp gene of *S. suis* (Smith et al., 1992), which is highly expressed in vivo as well as in vitro, drives expression of the erythromycin-resistance gene. The control plasmid, pIVS-E, does not contain a promoter in front of the erythromycin-resistance gene. The strains were inoculated intravenously or intranasally. All pigs infected with strain 10 (pIVS-PE) showed specific *S. suis* symptoms (Table 3) and, except for one, all pigs died in the course of the experiment. Moreover, high numbers of bacteria were isolated from the central nervous system, the serosae and the joints. In contrast, none of the pigs inoculated with strain 10 (pIVS-E) showed specific clinical signs of disease and all survived the infection until the end of the experiment. Moreover, bacteria were not isolated from the central nervous system, the serosae or the joints of these animals. These data demonstrated that in vivo-expressed sequences could be selected from pigs using the applied antibiotic treatment regimen.

Selection of Gene Sequences Expressed in Vivo in Piglets.

Piglets were inoculated intravenously with different doses (5×10$^5$ to 5×10$^8$ c.f.u.) of the *S. suis* library (Table 3) and treated with erythromycin as described herein. Specific signs of disease developed in all animals three to eight days after infection (Table 3). High numbers of bacteria were recovered from tissues (central nervous system, joints, serosae, lung, liver, spleen, heart and kidney) of the individual piglets. Analysis of the recovered bacteria showed that a limited number of different clones were present in each of the bacterial samples isolated from the diseased pigs. For example, 30 randomly selected clones from the joints of one pig all possessed identical DNA inserts as assessed by PCR and DNA sequence analysis (results not shown). In addition, at 80% of the 62 sample sites analyzed, four randomly selected clones were identical. However, from different tissues of a single animal, different clones or mutants could be isolated. On the other hand, identical clones could be isolated from different, as well as from corresponding, tissues of different animals. These findings indicated that a limited number of clones had been selected in vivo and were greatly enriched in the affected tissues. The observed selection was not tissue specific. Further, none of the selected clones failed to grow on agar plates that contained 1 µg erythromycin ml$^{-1}$.

Two-hundred forty-five clones were analyzed by PCR and partial sequence analysis. Among these, 22 unique ivs clones were found. The 22 sequences were analyzed for similarity to sequences of known genes by comparison with the GenBank/EMBL and SWISSPROT databases (Table 4). The sequences of two genes showed similarity to genes encoding putative virulence factors: ivs21, 26 and 30 which was identical to the epf gene, a previously identified *S. suis* gene, putatively involved in virulence (Smith et al., 1993; Smith et al., 1996); and ivs31 (SEQ ID NO: 37), which was similar to the fibronectin-binding protein of *S. gordonii*. Moreover, the sequences of two ivs genes (ivs25 (SEQ ID NO: 24) and ivs6, 7, 13 and 14 (SEQ ID NO: 43)) were homologous to two environmentally regulated ivi genes, previously identified using IVET selection in other bacterial species (Camilli and Mekalanos, 1995; Lowe et al., 1998). Four ivs sequences (ivs25 (SEQ ID NO: 34); ivs23 and 24 (SEQ ID NO: 33), ivs2, 4 and 28 (SEQ ID NO: 31); and ivs6, 7, 13 and 14 (SEQ ID NO: 43)) were also found when the library was selected using iron-restricted conditions. The remainder of the sequences showed similarity to sequences of known, non-*S. suis* genes, including two genes showing similarity to mobile elements and five genes showing similarity to genes of unknown function.

The identification of environmentally regulated genes of *S. suis* serotype 2 by the use of iron-restricted conditions and by experimental infection of piglets is described. Eighteen unique iri genes and 22 unique ivs genes were found. None of the ivs genes was exclusively expressed in vivo. Four iri genes were identical to four clones selected in vivo. The selected gene sequences encode for potential virulence factors, expand our knowledge about the pathogenesis of *S. suis* infections in pigs and are of value in control of the disease either by the development of effective vaccines or by the development of new diagnostic methods. A promoter trap was used to identify environmentally regulated *S. suis* genes expressed under specific conditions, i.e., during iron-restriction or during experimental infection. This system differs from the antibiotic-based IVET system described for *S. typhimurium* (Mahan et al., 1995) in two ways. One is that the lacZ reporter gene fusion is omitted in our vector constructions because inclusion of the lacZ gene resulted in structural instability of the vector. The other difference is that a plasmid system was used rather than a chromosomal integration system. A plasmid system was used because the low transformation efficiency of *S. suis* (Smith et al., 1995) might prevent the generation of a complete gene library using a chromosomal integration system.

From the data, it is evident that a number of inducible and environmentally regulated sequences were selected. Four iri genes were identical to four ivs genes. Because most bacteria require iron for their growth and because there is a limited amount of free iron available within the host (Payne, 1993), it might be expected that the expression of some ivs genes is regulated by iron. With the in vivo selection system, tissue-specific colonization was not observed: clones isolated from one piglet were also isolated from other piglets from corresponding as well as from different tissues. This might be due to the mechanisms involved in the molecular pathogenesis of *S. suis* infections in pigs. Furthermore, it was striking and different from the observations made with IVET systems that only a limited number of clones could be selected. In addition, we were not able to demonstrate that we selected for gene sequences that are exclusively expressed in vivo. This could be explained either by the absence of promoter sequences exclusively expressed in vivo among the 22 identified ivs genes, and/or by the inability of this plasmid-based system to identify such sequences due to gene dose effects.

A number of interesting genes were selected. Two ivs genes showed similarity to genes encoding putative virulence factors. Ivs21, 26 and 30 were shown to be identical to the epf gene of *S. suis* (Smith et al., 1993), which is found in virulent strains of *S. suis* serotypes 1 and 2 (Stockhofe-Zurwieden et al., 1996; Vecht et al., 1991; Vecht et al., 1992). Ivs31 (SEQ ID NO: 37) showed similarity to the fibronectin/fibrinogen-binding protein of *S. gordonii* (accession no. X65164) and group A Streptococci (Courtney et al., 1994). In Streptococci, fibronectin/fibrinogen-binding proteins play an important role in adhesion to host cells and are considered to be important virulence factors. The selection of these two ivs genes demonstrated the selectivity of the system and might be indicative for the relevance of the other ivs genes in the pathogenesis of *S. suis* infections in pigs. The performance of the system was further demonstrated by the observation that two ivs genes, ivs25 (SEQ ID NO: 34) and ivs6, 7, 13 and 14 (SEQ ID NO: 43) showed similarity to environmentally regulated genes previously identified using an IVET selection system in other bacterial species.

Ivs25 (SEQ ID NO: 34) showed significant similarity to the sapR gene of *S. mutans* (accession no. P72485) and *Lactobacillus sake* Lb706 (Axelsson and Holck, 1995) as well as to the agrA gene of *S. aureus* (Projan and Novick, 1997), both of which encode response regulator proteins of bacterial two-component signal-transduction systems, thus mediating the response to an environmental signal (Projan and Novick, 1997). Use of an IVET selection system for *S. aureus* in mice selected the region preceding the agrA gene, suggesting induction of agrA expression under in vivo conditions (Lowe et al., 1998). Moreover, in *S. aureus*, the agr locus was shown to play an important role in altering the expression of a considerable number of virulence factors in response to cell density (Projan and Novick, 1997).

Clones ivs6, 7, 13 and 14 (SEQ ID NO: 43) showed similarity to a gene, iviVI, previously identified by IVET selection in *V. cholerae* (Camilli and Mekalanos, 1995). The function of iviVI is unknown. However, the genes showed similarity to members of the ATP-binding cassette family of transporters. The sequenced portion of ivs6, 7, 13 and 14 (SEQ ID NO: 43) included an N-terminal ATP-binding Walker A box motif, which is highly conserved in this transporter family.

Four ivs genes were identical to four iri genes. The first gene, ivs23 and 24 (SEQ ID NO: 33), which is identical to iri24 (SEQ ID NO: 17), showed similarity to cpsY of *S. agalactiae* (Koskiniemi et al., 1998) and to oxyR of various organisms (Demple, 1999). CpsY of *S. agalactiae* is involved in the regulation of capsule expression and environmental induction of expression of the cpsY gene has been suggested by Koskiniemi et al. (1998). In *S. suis*, ivs23 and 24 (SEQ ID NO: 33). and iri24 (SEQ ID NO: 17) are not linked to the capsular locus (Smith et al., 1999). The oxyR gene is the central regulator of oxidative stress response in *E. coli* (Demple, 1999) and approximately ten genes are under the control of the OxyR protein. The second gene, ivs2, 4 and 28 (SEQ ID NO: 31), which is identical to iri10 and 20 (SEQ ID NO: 9), showed similarity to the yoaE gene of *E. coli* (accession no. P76262), a putative ABC transporter protein. The third and the fourth genes, ivs25 (SEQ ID NO: 34) and ivs6, 7, 13 and 14 (SEQ ID NO: 43) were identical to iri1, 6 and 22 (SEQ ID NO: 8) and iri2 (SEQ ID NO: 15), respectively. These genes also showed similarity to ivi genes selected using IVET in other bacterial species.

Based on data presented by Niven et al. (1999), selection of iri genes of *S. suis* is not expected. The authors described that *S. suis* does not require iron for growth. However, in their studies the authors used media reduced from iron by using ethylenediamine di-o-hydroxyphenylacetic acid (EDDA). Therefore, the different conditions used in vitro may explain the different results obtained.

Two of the *S. suis* ivs genes, ivs1 (SEQ ID NO: 25) and ivs8 (SEQ ID NO: 44), showed similarity to transposon sequences. Moreover, one *S. suis* ivs gene, ivs2, 4 and 28 (SEQ ID NO: 31), had a GC % that was considerably higher than the composition of the rest of the selected genes. It is striking that in *S. typhimurium*, several of the ivi clones that are required for full virulence have been found to be associated with mobile elements. Their atypical base composition and codon usage has led to the suggestion that they have been acquired from other bacterial species by horizontal transfer (Conner et al., 1998).

Our screen also identified five ivs genes that showed similarity to sequences encoding proteins of unknown function. These genes are not standard housekeeping or metabolic genes.

Besides the four ivs/iri genes, a considerable number of other iri genes have been selected in this study by plating the library under iron-restricted conditions. Interestingly, one of the selected iri genes, iri31, is identical to the cps2A gene of *S. suis*. This gene was previously isolated as a part of the capsular locus of *S. suis* serotype 2 (Smith et al., 1999) and was implicated in the regulation of capsular polysaccharide biosynthesis (Kolkman et al., 1997; Smith et al., 1999). Moreover, because the capsule of *S. suis* is expressed in larger size after in vivo growth when compared to growth in vitro (Quessy et al., 1994), regulated expression of cps2A might be expected. Another iri gene, iri7 (SEQ ID NO: 23), showed similarity to the rpgG gene of *S. mutans*. This gene was shown to be required for the biosynthesis of rhamnose-glucose polysaccharide (Yamashita et al., 1999). Because rhamnose is part of the polysaccharide capsule in *S. suis* serotype 2 (Elliott and Tai, 1978), a role of the iri7 (SEQ ID NO: 23) gene in capsule biosynthesis can be proposed. Iri34 (SEQ ID NO: 21) showed similarity to the np 16 gene, previously identified using IVET selection in *P. aeruginosa* and suspected to encode threonine dehydratase activity (Wang et al., 1996). Together with the observation that 4 iri genes could be selected by the in vivo approach, these data show that the iri genes encode important virulence factors for *S. suis*.

Contribution of Fibronectin-Binding Protein to Pathogenesis of *Streptococcus suis* Serotype 2.

*Streptococcus suis* causes severe infections, such as meningitis, septicemia, and arthritis, in piglets. The animals often do not survive the infection (6, 28). Occasionally, *S. suis* causes septicemia and meningitis in humans (3). The pathogenesis of an *S. suis* infection is rarely understood. Sows are symptomless carriers of *S. suis* on their tonsils and pass the bacteria on to their piglets. The piglets cannot cope with the bacteria and subsequently develop the specific symptoms of an *S. suis* infection. Until now, 35 capsular serotypes of *S. suis* have been described (26), but serotype 2 strains are most often isolated from diseased piglets. The capsule is an important virulence factor since piglets infected with an acapsular mutant of *S. suis* serotype 2 strains do not develop any clinical symptoms (22). Bacterial proteins have been suggested to play a role in the pathogenesis as well (2, 26). The expression of murimidase-released protein (MRP), extracellular factor (EF) and suilysin was shown to be strongly associated with pathogenic strains of *S. suis* serotype 2 (1, 29, 30). Since isogenic mutants lacking MRP and EF and isogenic mutants lacking suilysin were still pathogenic in young piglets, these proteins are not absolutely required for virulence (2, 23). Recently, a new virulence factor was identified (21) by using a complementation approach. The function of this virulence factor in the pathogenesis has to be further investigated.

Many important virulence factors are environmentally regulated and are induced at specific stages of the infection process (15). To identify these genes in *S. suis*, promoters and their downstream sequences that are "on" during experimental *S. suis* infection of piglets (20) were cloned. Twenty-two in vivo selected (ivs) genes were found. Two of the ivs genes were directly linked to virulence since homology was found to genes in the database that encode for known virulence factors. One of these ivs genes (ivs-21) was identical to the epf gene of virulent *S. suis* serotype 2 strains (30). The other (ivs-31) (SEQ ID NO: 37) showed homology to genes encoding fibronectin-/fibrinogen-binding proteins of *Streptococcus gordonii* (GenBank accession no. X65164) and *Streptococcus pyogenes* FBP54 (8). A considerable number of fibronectin-binding proteins of various bacterial species have been shown to be important virulence factors (12). In *S. pyogenes*, FBP54 was shown to be expressed in the human host and to preferentially mediate adherence to human buccal epithelial cells (7). It was shown that the FBP54 protein induces protective immunity against *S. pyogenes* challenge in mice (13).

A fibronectin-/fibrinogen-binding protein of *S. suis* (FBPS) is described herein and the sequence of fbps was determined. Binding studies showed that purified FBPS bound fibronectin and fibrinogen. A contribution of FBPS to the pathogenesis of *S. suis* serotype 2 was found.

Materials and Methods.

Bacterial Strains and Growth Conditions. The bacterial strains and plasmids used in this study are listed in Table 5. *S. suis* strains were grown in Todd-Hewitt broth (code CM 189; Oxoid, Ltd.) and plated on Columbia blood base agar plates (code CM331; Oxoid, Ltd., London, United Kingdom), containing 6% (vol/vol) horse blood. *E. coli* strains were grown in Luria Broth (17) and plated on Luria Broth containing 1.5% (wt/vol) agar. If required, antibiotics were added at the following concentrations: 50 µg/ml of spectinomycin (Sigma, St. Louis, Mo.) for *E. coli* and 100 µg/ml for *S. suis*, 100 µg/ml of ampicillin (Boehringer, Mannheim, Germany) for *E. coli* and 25 µg/ml of kanamycin (Boehringer) for *E. coli*.

DNA Techniques and Sequence Analysis. Routine DNA manipulations were performed as described by Sambrook et al. (19). DNA sequences were determined on a 373A DNA Sequencing System (Applied Biosystems, Warrington, Great Britain). Samples were prepared by use of an ABI Prism dye terminator cycle sequencing ready reaction kit (Applied Biosystems). Sequencing data were assembled and analyzed using the Lasergene program (DNASTAR). The BLAST software package was used to search for protein sequences homologous to the deduced amino acid sequences in the GenBank/EMBL databases.

Southern Blotting and Hybridization. Chromosomal DNA was isolated as described by Sambrook et al. (19). DNA fragments were separated on 0.8% agarose gels and transferred to GeneScreen Plus hybridization transfer membrane (NEN™ Life Science Products, Boston, USA) as described by Sambrook et al. (19). DNA probes of the fbps and spc genes were labeled with ($\alpha$-$^{32}$P)dCTP (3,000 Ci/mmol; Amersham Life Science, Buckinghamshire, Great Britain) by use of a random primed DNA labeling kit (Boehringer). The DNA on the blots was pre-hybridized for at least 30 minutes at 65° C. and subsequently hybridized for 16 hours at 65° C. with the appropriate DNA probes in a buffer containing 0.5 M sodium phosphate (pH 7.2), 1 mM EDTA and 7% sodium dodecyl sulphate. After hybridization, the membranes were washed twice with a buffer containing 40 mM sodium phosphate (pH 7.2), 1 mM EDTA and 5% sodium dodecyl sulphate for 30 minutes at 65° C. and twice with a buffer containing 40 mM sodium phosphate (pH 7.2), 1 mM EDTA and 1% sodium dodecyl sulphate for 30 minutes at 65° C. The signal was detected on a phosphor-imager (Storm; Molecular Dynamics, Sunnyvale, Calif.).

Construction of a fbps Knock-Out Mutant. To construct the mutant strain 10ΔFBPS, the pathogenic strain 10 (27, 29) of *S. suis* serotype 2 was electrotransformed (24) with the plasmid pFBPS7-47. In this plasmid, the fbps gene was inactivated by the insertion of a spectinomycin-resistance gene. To create pFBPS7-47 (FIG. 1), the 382 bp SalI-SalI fragment of pFBPS7-46 was replaced by the 1.2 kb EcoRV-SmaI fragment of pIC-Spc, containing the spectinomycin resistance gene, after the SalI sites of the vector were made blunt (FIG. 1). After electrotransformation of strain 10 with pFBPS7-47, spectinomycin-resistant colonies were selected on Columbia agar plates containing 100 µg/ml of spectinomycin. Southern blotting and hybridization experiments were used to select for double cross-over integration events (data not shown).

FBPS Expression Construct. To construct an FBPS expression plasmid, the QIAexpress Kit (Qiagen GmbH, Hilden, Germany) was used. The primers corresponded to positions 250 to 272 and from 1911 to 1892 of the fbps gene. The sequences of these primers were 5'(GCGGATCCGATGAC-GATGACAAATCTTTTGACGGATTTTTTTTAC)3' (SEQ ID NO: 46) and 5'(CCCAAGCTTGGGCATGAACTA-GATTTTCATGG)3' (SEQ ID NO: 47). The primers contained restriction sites for BamHI and HindIII, respectively, to amplify the fbps gene from pFBPS7-47. The amplified PCR product was digested with BamHI and HindIII and the 1.8 kb fbps gene was cloned into pQE-30 digested with BamHI and HindIII, yielding pQE-30-FBPS. pQE-30-FBPS was transformed to M15 (pREP4).

Purification of FBPS. M15 (pREP4) (pQE-30-FBPS) was used to express and purify the FBPS using the QIAexpressionist™ (Qiagen). In short, M15 (pREP4) (pQE-30FBPS) cells were grown exponentially; 1 mM IPTG was added and the cells were allowed to grow another four hours at 37° C. Subsequently, cells were harvested and lysed. The cleared supernatants were loaded onto $Ni^{2+}$-NTA agarose columns. FBPS containing a 6×HIS tag was bound to the $Ni^{2+}$-column. The columns were washed and the protein was eluted. Different buffers were used for native and for denaturing purification. FBPS purified under denaturing conditions was renaturated on a $Ni^{2+}$-NTA column by using a linear 6 M-1 M urea gradient in 500 mM NaCl, 20% glycerol and 20 mM Tris-HCl (pH7.4), containing protease inhibitors (25 µg/ml of pefabloc, 0.7 µg/ml of pepstatin, 1 µg/ml of aprotinin, 0.5 µg/ml of leupeptin). All procedures were performed according to the manufacturer's recommendations. The 6×HIS tag was removed from the protein by incubating purified FBPS in 20 mM Tris-HCl (pH 7.4), 50 mM NaCl, 2 mM $CaCl_2$ and 0.5 U of light chain enterokinase (New England Biolabs, Beverly, Mass.) for 16 hours at RT.

Immunization of Rabbits with FBPS. Purified and renaturated FBPS was used to immunize two rabbits. To remove urea, the protein was dialyzed against phosphate buffered saline (136 mM NaCl; 2.68 mM KCl; 8.1 mM $Na_2HPO_4$; 2.79 mM $KH_2PO_4$ (pH 7.2)) over night at 4° C. Seven days before immunization, blood was collected from the rabbits to determine the natural titers against FBPS. At day one, those rabbits with negative anti-FBPS titers were immunized intramuscularly with two times 0.5 ml of 100 µg/ml of FBPS in a water-in-oil emulsion (Specol; ID-Lelystad). At day 28, rabbits were immunized for the second time using the same amount of protein and the same route of immunization. Three weeks after the second immunization, the rabbits were sacrificed and blood was collected. The blood was coagulated and serum was collected and used for immunodetection of FBPS.

Immunodetection of FBPS. Proteins were separated by sodium dodecyl sulfate (SDS)-polyacrylamide gel electrophoresis (PAGE) by standard procedures (19). Proteins in the gel were visualized using SYPRO-orange (Molecular Probes, Sunnyvale, Calif.) staining according to the manufacturer's recommendations. Signals were detected on a phosphor imager (Storm; Molecular Dynamics). A known bovine serum albumin concentration range was used as a standard to calculate the amounts of protein present in the gel. The Molecular Dynamics program was used for the calculations.

Proteins were transferred to a nitrocellulose membrane by standard procedures (19). The membranes were blocked in Blotto: Tris-buffered saline (TBS) (50 mM Tris-HCl (pH 7.5), 150 mM NaCl) containing 4% skimmed milk and 0.05% Tween 20 at room temperature (RT) for one hour. To detect recombinant purified FBPS, membranes were incubated with a monoclonal antibody against the 6×HIS tag (Clontech, Palo Alto, Calif.) in a 1:10,000 dilution in Blotto-TBS (1:1) at RT for one hour, followed by an incubation with alkaline phosphatase-conjugated anti-mouse antibody in a 1:1,000 dilution in Blotto-TBS (1:1) at RT for one hour. Reactivity of purified FBPS was tested by using a convalescent serum of a pig that had survived an S. suis infection. Nitrocellulose membranes were incubated with the polyclonal pig serum in a 1:200 dilution in Blotto-TBS (1:1) at RT for one hour, followed by incubation at RT for one hour with alkaline phosphatase-conjugated anti-swine antibody in a 1:2,000 dilution in Blotto-TBS (1:1). As a substrate, Nitro Blue Tetrazolium (Merck, Darmstadt, Germany) bromochloroindolyl phosphate (Sigma) was used. All washing steps were performed in Blotto-TBS (1:1).

Fibronectin and Fibrinogen Binding. Binding studies were performed by indirect Western blotting. Proteins were separated by SDS-PAGE and transferred to a nitrocellulose membrane as described herein. The membranes were blocked in MPBS: PBS containing 4% skimmed milk and 0.05% Tween 20. Subsequently, the membrane was incubated with 5 µg/ml of human fibronectin (fn) (Sigma) or 5 µg/ml of human fibrinogen (fgn) (Sigma) in PBS containing 5% fetal calf serum, 2% NaCl, and 0.05% Tween 80 at RT for one hour. To detect bound fibronectin and fibrinogen, the membranes were incubated with horse-radish peroxidase-conjugated anti-fibronectin (DAKO) or anti-fibrinogen (DAKO) antibodies in a 1:1,000 dilution in PBS containing 5% fetal calf serum, 2% NaCl, and 0.05% Tween 80 at RT for one hour. The signal was visualized by using $ECL^+$ (Amersham Pharmacia Biotech, N.J.) according to the manufacturer's recommendations. Signals were detected on a phosphor imager (Storm; Molecular Dynamics). All washing steps were performed in MPBS-PBS (1:1).

Experimental Infections. Germ-free piglets, cross-breeds of Great Yorkshire and Dutch Landrace, were obtained from sows by cesarean section. The surgery was performed in sterile flexible film isolators. Piglets were allotted to groups of four and were housed in sterile stainless steel incubators. Housing conditions and feeding regimens were as described (27, 29). Six-day-old piglets were inoculated intranasally with about $10^7$ cfu of Bordetella bronchiseptica 92932 to predispose the piglets to infection with S. suis. Two days later, the piglets were inoculated intranasally with $10^6$ cfu of S. suis strain 10 plus $10^6$ cfu of S. suis strain 10ΔFBPS. To determine differences in virulence between wild-type and mutant strains, $LD_{50}$ values should be determined. To do this, large numbers of piglets are required. For ethical reasons, this is not acceptable. To circumvent this problem, co-colonization studies were performed.

To monitor for the presence of S. suis and B. bronchiseptica and to check for absence of contaminants, swabs taken from the nasopharynx and the feces were cultured three times a week. The swabs were plated directly onto Columbia agar containing 6% horse blood or grown for 48 hours in Todd-Hewitt broth and subsequently plated onto Columbia agar containing 6% horse blood. Pigs were monitored twice a day for clinical signs and symptoms, such as fever, nervous signs, and lameness. Blood samples from each pig were collected three times a week. Leukocytes were counted with a cell counter. The piglets were killed when specific signs of an S. suis infection were observed, such as arthritis or meningitis, or when the pigs became mortally ill. The other piglets were killed two weeks after inoculation with S. suis and examined the same way as the piglets that were killed based on their clinical symptoms. All piglets were examined for pathological changes.

Tissue specimens from heart, lung, liver, kidney, spleen, and tonsil, and from the organs specifically involved in an S. suis infection (central nervous system (CNS), serosae, and joints) were sliced with a scalpel or a tissuenizer. Tissue slices from each organ or site were resuspended in 2-25 ml of Todd-Hewitt containing 15% glycerol depending on the size of the tissue slice. The suspension was centrifuged at 3,000 rpm for five minutes. The supernatant was collected and serial dilutions were plated on Columbia agar containing 6% horse blood, as well as on Columbia agar plates containing 6% horse blood and 100 µg/ml of spectinomycin to quantitate the number of wild-type and mutant bacteria present. The number of mutant strain 10ΔFBPS cells was determined by counting the number of CFU on the appropriate serial dilution on the selective plates; the number of wild-type strain 10 cells was determined by counting the number of CFU on the appropriate serial dilution on the Columbia Agar blood plates of which the number of CFU counted on the selective plates was subtracted. When wild-type and mutant bacteria were found in tissues, the ratio of wild-type and mutant strain was determined again by toothpicking about 100 individual colonies onto both Columbia Agar plates and onto Columbia Agar plates containing 100 µg/ml spectinomycin.

All animal experiments were approved by the ethical committee of the Institute for Animal Science and Health in accordance with the Dutch law on animal experiments.

Nucleotide Sequence Accession Number. The nucleotide sequence data fbps have been submitted to GenBank, in which the sequence is listed under accession no. AF438158.

Results.

Cloning of the S. suis fbps Gene. One of the in vivo selected genes (ivs-31) (SEQ ID NO: 37) (20) showed homology to the 5' part of genes encoding for FlpA and FBP54, fibronectin-binding proteins (FnBP) of Streptococcus gordonii (GenBank accession no. X65164) and Streptococcus pyogenes (8), respectively. To clone the entire fbps gene of S. suis, ivs31 (SEQ ID NO: 37) was used as a probe to identify a chromosomal DNA fragment of S. suis serotype 2 containing flanking fbps sequences. A 5 kb EcoRI fragment was identified and cloned in pGEM7Zf(+) yielding pFBPS7-46 (FIG. 1). Sequence analysis revealed that this fragment contained the entire fbps gene of S. suis serotype 2.

An open reading frame of 1659 bp coding for a polypeptide of 553 amino acids was found. The putative ATG start codon is preceded by a sequence similar to ribosome binding sites of gram-positive bacteria. Further upstream, two putative promoter sequences could be identified. Upstream of these promoter sequences of fbps, a direct repeat was found that could serve as a transcription terminator of the gene located 5' of fbps. Downstream of fbps, a gene that showed homology to an alpha-acetolactate decarboxylase was found. This gene is transcribed in the opposite direction of fbps. The deduced amino acid sequence was aligned with that of several previously identified FnBPs from other bacteria. As expected, FBPS was substantially homologous to FlpA of S. gordonii (76%) and also showed homology to FnBP's of other organisms, like Streptococcus pneumoniae (73%), S. pyogenes (69%), Lactococcus lactis (59%), and Bacillus subtilis (41%). Compared to the sequence of FBP54, FBPS has a longer N-terminus with 76 additional amino acids. This longer N-terminus was also seen in other organisms like S. gordonii, S. pneumoniae and B. subtilis. In FBP54, the primary fibronectin-/fibrinogen-binding domain was localized to its N-terminal part, to the first 89 amino acids (8). Over this region, the homology of FBPS to FBP54 is very high (80%), suggesting that FBPS can bind both fibronectin and fibrinogen.

Figure 2:
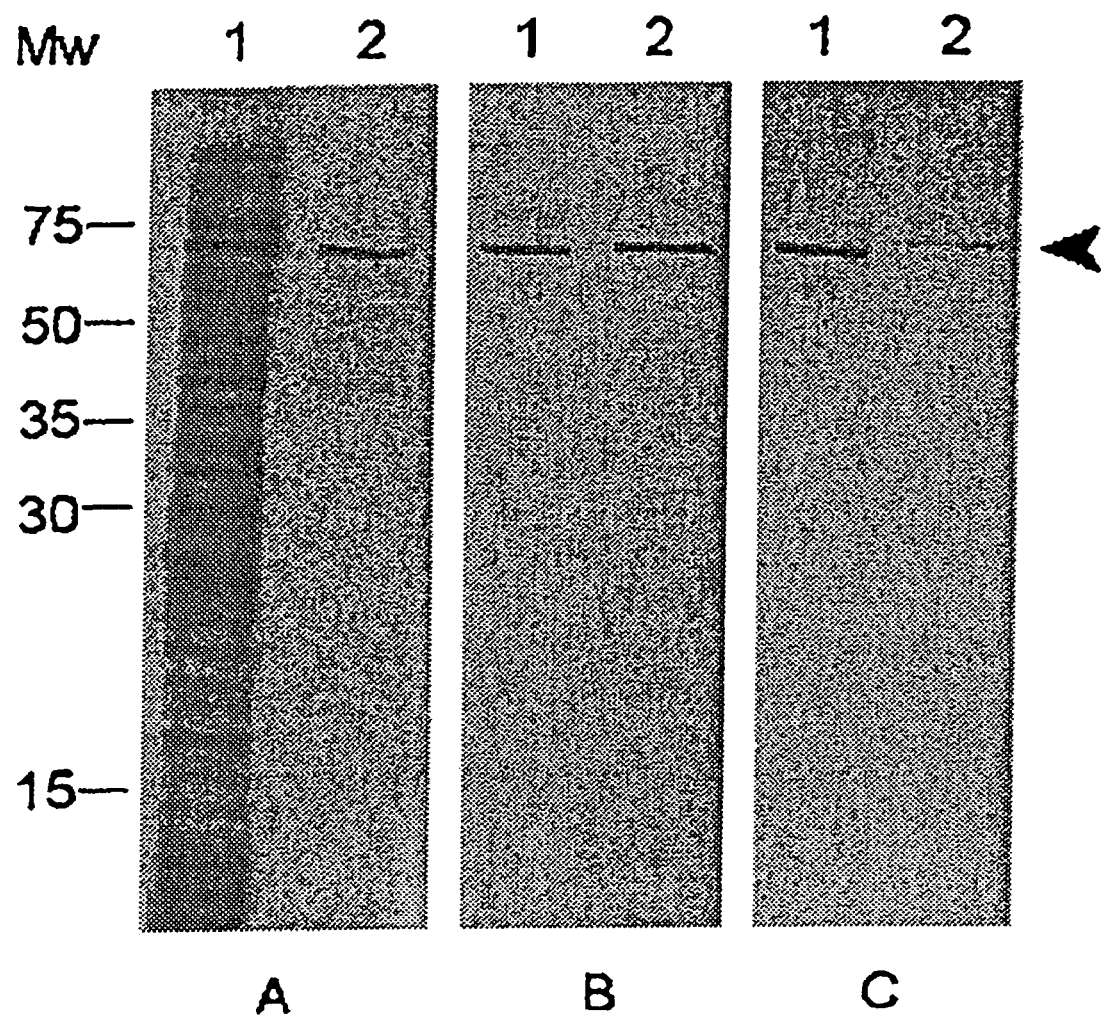
FIG. 2 shows purity and immunogenicity of FBPS purified under native conditions. SDS-PAGE analysis with SYPRO orange, a non-specific protein-staining (panel A) and Western blot analysis with a monoclonal antibody against the 6×HIS tag (panel B) of 4:1 of E. coli M15 (pQE-3O-pREP4-FBPS) lysate (lanes 1) and 165 ng of purified FBPS (lanes 2). Convalescent serum raised against S. suis strain 10 was used to test immunogenicity of FPBS present in 4:1 of E. coli M15 (pQE-30-pREP4-FBPS) lysate and 0.5 µg of purified FBPS (Panel C, lanes 1 and 2). Arrowhead, 64 kDa FPBS; Mw, molecular weight marker.

Binding of FBPS to Fibronectin and Fibrinogen. To confirm the binding of FBPS of S. suis to fibronectin (fn) and fibrinogen (fgn), FBPS was purified under native conditions. A protein expression construct, which expresses FBPS with a 6×HIS tag fused to the N-terminus, was used for purification. Four hundred µg of FBPS was purified from 50 ml of exponential-phase E. coli cells after induction with IPTG. The purity of this FPBS was determined with SDS-PAGE and Western blotting (FIG. 2). The induced E. coli lysate contained a broad range of proteins, among which the 64 kDa protein FBPS was present (panel A, lane 1). After purification, highly purified FBPS with 6×HIS tag was obtained (panel A, lane 2). When both samples were incubated with a monoclonal antibody against the 6×HIS tag, FBPS was the only protein that was detected (panel B).

Figure 3:
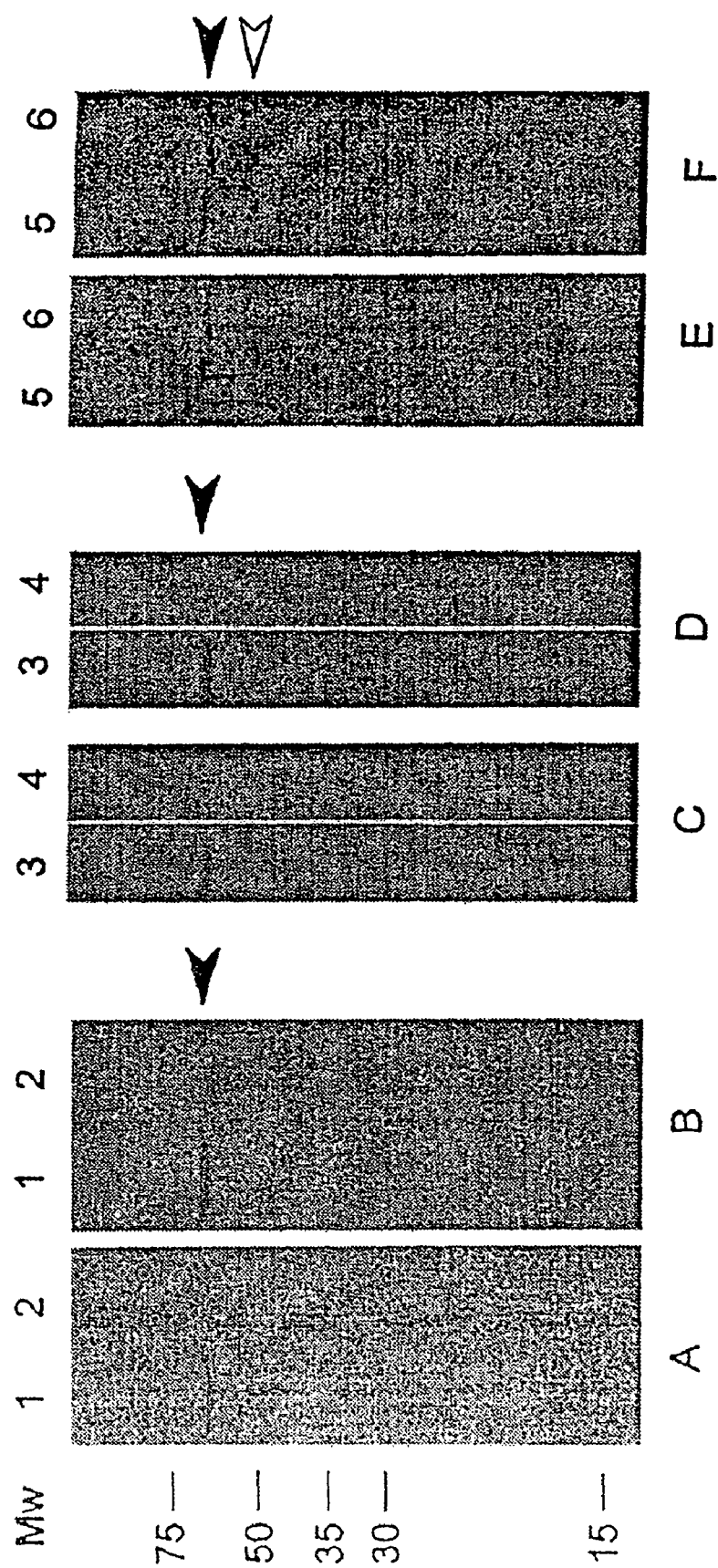
FIG. 3 depicts the binding studies with purified FBPS. Panels A and B were probed with 5 µg/ml of fn (A) or fgn (B). Lanes 1 contain 500 ng of purified FBPS, lanes 2 contain 500 ng of BSA. Panels C and D, lanes 3 and 4 contain 500 ng of purified FBPS. Lanes 3 were probed with 20 µg/ml of fn (C) or fgn (D), lanes 4 were incubated with conjugate without fn or fgn. Panels E and F were probed with 20 µg/ml of fn (E) or fgn (F). Lanes 5 contain 1.8 µg of purified FBPS digested with enterokinase, lanes 6 contain 500 ng of purified FBPS. The closed arrowhead indicates 64 kDa FBPS; the open arrowhead indicates approximately 55 kDa FBPS without 6×HIS.

To determine whether FBPS binds fn and fgn, a Western blot containing purified FBPS was incubated with soluble human fn and human fgn (FIG. 3, panels A and B). Specific binding of fn and fgn to FBPS was detected. No binding of fn and fgn to BSA, a negative control protein, was observed. To exclude possible background signals due to immunoglobulin-binding of FBPS, the same experiment was performed without addition of fibronectin or fibrinogen. No binding was found (FIG. 3, panels C and D) indicating that the binding was specific for fibronectin and fibrinogen. To control whether the binding of fn and fgn to FBPS was not mediated by the 6×HIS tag, the tag was removed by an enterokinase treatment. FIG. 3, panels E and F, show that FBPS without the 6×HIS tag still efficiently bound to fn and fgn. Therefore, it appears that FBPS can specifically bind to fn and fgn.

Immunogenicity of FBPS. Since it was shown that FBP54 induced a protective immune response in mice against a lethal dose of S. pyogenes (13), it was determined whether purified FBPS was recognized by convalescent serum of a pig that survived an S. suis infection. As shown in FIG. 2 panel C, the FBPS reacted with this anti-serum. When the same experiment was performed with non-immune serum of an SPF piglet, no band of the size of FBPS was detected (data not shown). These findings indicate that FBPS is expressed in vivo and that the protein is indeed immunogenic in young pigs.

Figure 4:
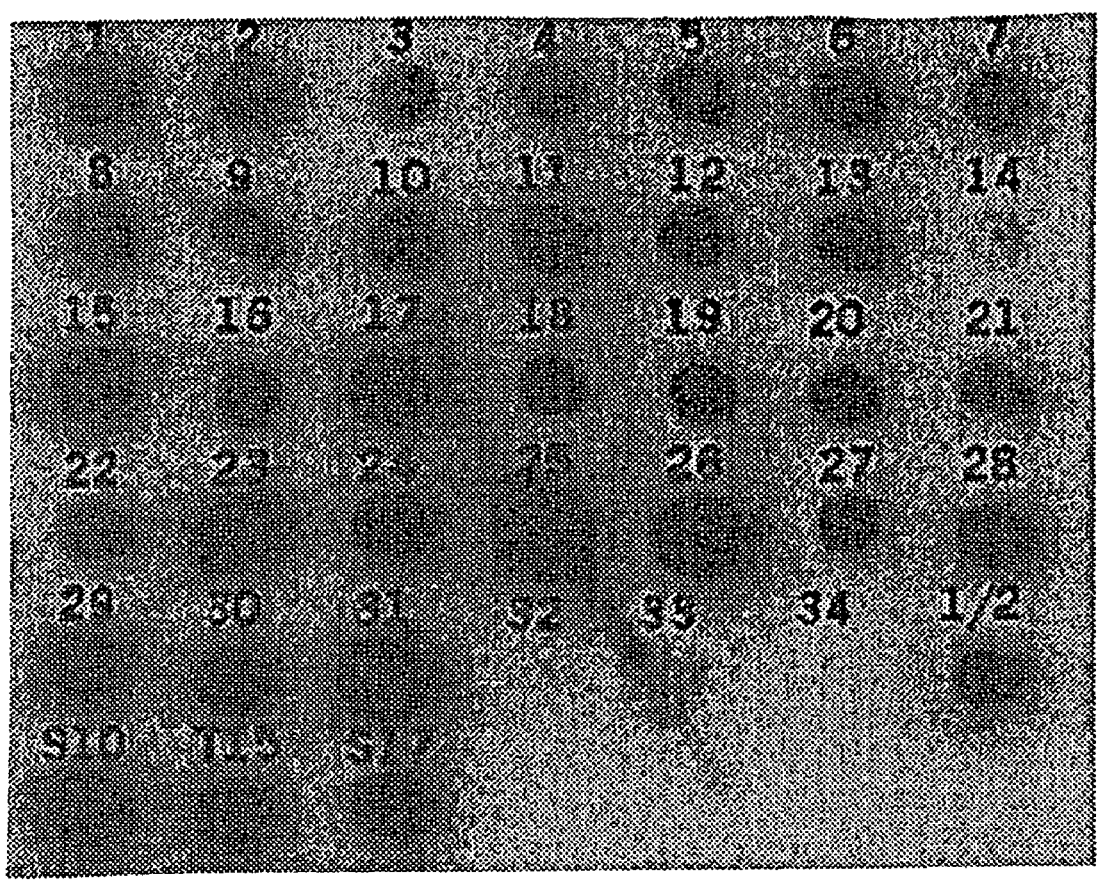
FIG. 4 shows the distribution of fbps among various S. suis serotypes. 1 µg of chromosomal DNA was spotted onto nitrocellulose membrane and hybridized with a $^{32}$P-labelled fbps probe. Serotypes were spotted as indicated. S10: S. suis serotype 2, MRP$^+$EF$^+$; T15: S. suis serotype 2 MRP$^-$EF$^-$; S17:S. suis serotype 2 MRP$^+$EF*.

Distribution of the fbps Gene Among the 35 S. suis Serotypes. Since we were interested in a cross-protective vaccine candidate, the presence of the fbps gene among the various S. suis serotypes was analyzed. Ivs-31 (SEQ ID NO: 37), the clone containing the promoter and the 5'-part of the fbps gene, was radiolabeled and chromosomal DNA of the reference strains of the 35 different S. suis serotypes was hybridized with this probe. The three different phenotypes of S. suis serotype 2, a pathogenic, a non-pathogenic and a weak pathogenic strain, were included in this study. The fbps gene was present in all S. suis serotypes and phenotypes except for serotypes 32 and 34 (FIG. 4).

Role of FBPS in Pathogenesis. To test the role of FBPS in the pathogenesis of S. suis, an isogenic knock-out mutant of FBPS was constructed in strain 10, strain 10ΔFBPS. Since upstream of fbps a direct repeat was found that could serve as a transcription terminator and downstream of fbps a gene showing homology to an alpha-acetolactate decarboxylase was found that is transcribed in the opposite direction, polar effects to genes upstream or downstream of fbps are not expected. To verify that the mutant strain 10ΔFBPS did not produce FBPS, protoplasts of strain 10 and strain 10ΔFBPS were subjected to SDS-PAGE and Western blotting. FBPS was detected using a polyclonal antiserum raised against purified FBPS. It was shown that strain 10ΔFBPS expressed no FBPS, while strain 10 did express FBPS (data not shown). Subsequently, the virulence of this mutant strain was tested in an experimental infection in piglets.

The mutant strain 10ΔFBPS was used in a competition challenge experiment with the wild-type strain to determine the relative attenuation of the mutant strain. Using in vitro conditions, the growth rates of the wild-type and mutant strain in Todd-Hewitt medium were found to be essentially identical (data not shown). Wild-type and mutant strain were inoculated at an actual ratio of 0.65 ($1.63 \times 10^6$ cfu of wild-type bacteria ml$^{-1}$ and $3.09 \times 10^6$ cfu of mutant bacteria ml$^{-1}$).

During the experiment, piglets that developed specific *S. suis* symptoms (meningitis, arthritis, or mortal illness) were killed. Piglets that did not develop these symptoms were killed at the end of the experiment. From all piglets, the ratio of wild-type and mutant strain in various organs was determined.

Figure 5B:
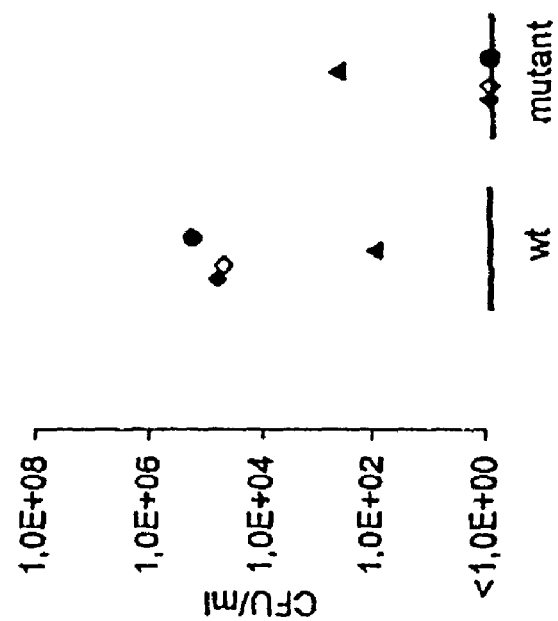
FIG. 5 illustrates the efficiency of colonization of wild-type and mutant bacteria on various organs of infected pigs. Panel A depicts colonization of the wild-type strain 10 and the mutant strain 10ΔFBPS of the tonsils. A closed diamond symbol is tonsil pig no. 4664; ■ tonsil pig no. 4665; ▲ tonsil pig no 4666; • tonsil pig no. 4668. Panel B depicts colonization of the specific organs. Open and closed diamond symbols are pus from joints pig no. 4664; ▲ pus from joint pig no. 4666; • CNS pig no. 4668. Each dot represents the numbers of wild-type or mutant bacteria isolated from one particular organ, from one piglet.
Figure 5A:
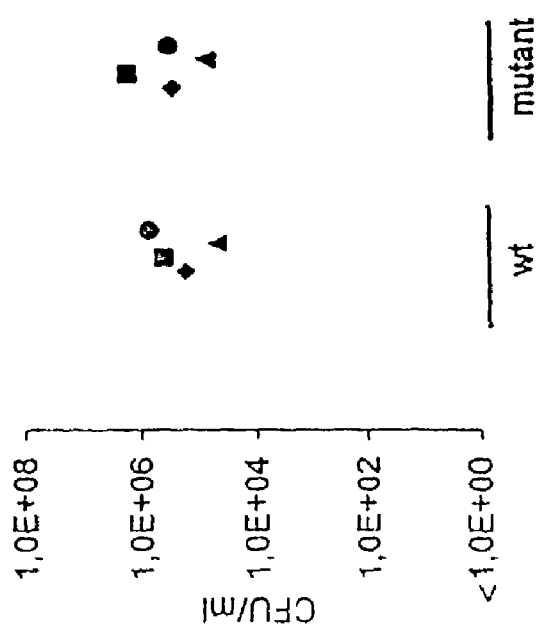

As shown in FIG. 5, panel A, similar numbers of wild-type and mutant bacteria were re-isolated from tonsils. The ratio was similar to the input ratio (ratio varied from 0.33-0.85, average 0.61). This indicates that the efficiency of colonization of wild-type and mutant strain on tonsils was essentially identical. Apparently, FBPS is not strictly required for colonization of the tonsils of the piglets. Three out of four piglets developed clinical signs specific for an *S. suis* infection. Two piglets (4664 and 4666) showed clinical signs of arthritis and one piglet (4668) showed clear central nervous signs. The fourth piglet did not develop any clinical signs. These observations coincided with pathomorphological abnormalities of the specific organs of an *S. suis* infection in post-mortem sections.

As shown in FIG. 5, panel B, exclusively wild-type bacteria were re-isolated from the joints of piglet 4664 and from the CNS of piglet 4668. The numbers of CFU of wild-type bacteria that were re-isolated from these specific organs were very high, while no mutant bacteria were found. From the joints of pig 4666, low numbers of both wild-type and mutant bacteria were re-isolated in a ratio of 0.84 ($1.0 \times 10^2$ CFU of wild-type bacteria and $5.2 \times 10^2$ CFU of mutant bacteria), a ratio essentially identical to the input ratio (FIG. 5, panel B). Southern blot experiments using the fbps and the spc genes as probes, confirmed that the mutant bacteria isolated from the joint of pig 4666 were indeed identical to the input mutant bacteria. Taken together, these data indicate, that the FBPS mutant is capable of reaching and colonizing the specific *S. suis* organs (at least the joints), but that the mutant is far less efficiently recovered from organs than the wild type.

TABLE 1

Bacterial strains and plasmids.

| Strain/plasmid | relevant characteristics* | source/reference |
|---|---|---|
| Strain | | |
| *E. coli* XL2 blue | | Stratagene |
| *S. suis* 10 | virulent serotype 2 strain | (Vecht et al., 1992) |
| Plasmid | | |
| pKUN19-spc | replication functions pUC, $Amp^R$, $Spc^R$ | (Konings et al., 1987, Smith et al., 1995) |
| pGKV210 | replication functions pWVO1, $Cm^R$, $Em^R$ | (Van der Vossen et al., 1987) |
| pE194 | $Em^R$ | (Horinouchi & Weisblum, 1987) |
| pMR11 | pKUN19 containing *S. suis* mrp gene | (Smith et al., 1992) |
| pIVS-E | replication functions pWVO1, $Spc^R$, promoterless emR gene of pE194 | this work |
| pIVS-PE | pIVS-E containing promoter of mrp preceding the promoterless emR gene | this work |
| pIVS-RE | pIVS-E containing random *S. suis* sequences preceding the promoterless emR gene | this work |

*$Spc^R$: spectinomycin resistant
$Em^R$: erythromycin resistant
$Amp^R$: ampicillin resistant
$Cm^R$: chloramphenicol resistant

TABLE 2

Iron-restriction induced *S. suis* genes.

| Clone | Insert (bp) | GC % | Data base homology (accession no.) | Function of homolog | % Identity |
|---|---|---|---|---|---|
| *Regulatory functions* | | | | | |
| iri 1, 6, 22 (SEQ ID NO: 8) | 800 | 34 | *S. mutans* SapR (U75483) | response regulator protein | 44 |
| | | | *S. aureus* AgrA (X52543) | response regulator protein | 51 |
| | | | *S. aureus* Ivi2 | | |
| iri 24 (SEQ ID NO: 17) | 850 | 38 | *S. agalactiae* CpsY (CAB36982) | regulation capsule expression | 46 |
| | | | *E. coli* OxyR (P11721) | oxidative stress regulator | 51 |
| iri 23 (SEQ ID NO: 16) | 1000 | 38 | *B. subtilis* YvyD (P28368) | sigma-54 modulator homologue | 44 |
| *Metabolic functions* | | | | | |
| iri 7 (SEQ ID NO: 23) | 800 | 39 | *S. mutans* RgpG (Q9XDW8) | rhamnose-glucose biosynthesis | 76 |
| iri 11 (SEQ ID NO: 10) | 700 | 34 | *L. lactis* NrdD (Q9ZAX6) | anaerobic ribonucleotide reductase | 51 |
| iri 14 (SEQ ID NO: 12) | 500 | 38 | *S. pneumoniae* SulB (Q54614) | dihydrofolate synthetase | 41 |
| iri 16 (SEQ ID NO: 13) | 850 | 48 | *B. subtilis* TrmU (O35020) | RNA methyltransferase | 62 |
| iri 32 (SEQ ID NO: 20) | 300 | 41 | *C. histolyticum* RuvB (O9ZNJ5) | hypoxanthine-guanine phosphoribosyl transferase | 55 |
| iri 34 (SEQ ID NO: 21) | 1000 | 44 | *L. lactis* IlvA (U92974) | probable threonine dehydratase | 56 |
| | | | *P. aeruginosa* Pn16 | | |
| *Transporter functions* | | | | | |
| iri 2 (SEQ ID NO: 15) | 750 | 36 | *B. subtilis* YloD (O34328) | putative guanylate kinase | 50 |
| | | | *S. gordonii* ComYA (U81957) | putative ABC transporter | 37 |
| | | | *Vibrio cholerae* IviVI (Q56605) | putative ABC transporter | 47 |

TABLE 2-continued

Iron-restriction induced *S. suis* genes.

| Clone | Insert (bp) | GC % | Data base homology (accession no.) | Function of homolog | % Identity |
|---|---|---|---|---|---|
| iri 10, 20 (SEQ ID NO: 9) | 1350 | 51 | *E. coli* YoaE (P76262) | putative transport protein | 94 |
| | | | Unknown | | |
| iri 13, 15, 27 (SEQ ID NO: 11) | 800 | 34 | *M. tuberculosis* MTCY336_33 hypothetical protein (O06593) | unknown | 38 |
| iri 29 (SEQ ID NO: 18) | 850 | 36 | *S. aureus* Yp15 (P13977) hypothetical protein | unknown | 39 |
| iri 18 (SEQ ID NO: 14) | 800 | 39 | *S. crista* hypothetical protein (AAF61316) | unknown | 82 |
| iri 3 (SEQ ID NO: 19) | 700 | 36 | no homology found | | |
| iri 4 (SEQ ID NO: 22) | 700 | 36 | no homology found | | |
| iri 8, 26 (SEQ ID NO: 24) | 900 | 35 | no homology found | | |

TABLE 3

Virulence of *S. suis* 10 (pIVET-E), 10 (pIVET-PE) and 10 (pIVET-RE) in gnotobiotic piglets.

| Strains/library | No. of piglets | Dose (route of infection) | Mortality * (%) | Morbidity ¥ (%) | Clinical index of the group ┆ Specific ‖ | Non-specific ¤ | Fever index à | Leukocyte index £ | No. of pigs from which *S. suis* was isolated CNS | Serosae | Joints |
|---|---|---|---|---|---|---|---|---|---|---|---|
| 10 (pIVS-E) | 4 | $10^6$ (i.n.) | 0 | 0 | 0 | 6 | 9 | 75 | 0 | 0 | 0 |
| 10 (pIVS-E) | 4 | $10^6$ (i.v.) | 0 | 0 | 6 | 12 | 31 | 0 | 0 | 0 | 0 |
| 10 (pIVS-PE) | 4 | $10^6$ (i.n.) | 100 | 100 | 30 | 40 | 35 | 100 | 3 | 0 | 2 |
| 10 (pIVS-PE) | 4 | $10^6$ (i.v.) | 75 | 100 | 50 | 42 | 43 | 50 | 3 | 3 | 4 |
| 10 (pIVS-RE) | 4 | $5 \times 10^5$ (i.v.) | 100 | 100 | 56 | 75 | 44 | 83 | 2 | 2 | 4 |
| 10 (pIVS-RE) | 4 | $5 \times 10^6$ (i.v.) | 100 | 100 | 43 | 73 | 43 | 60 | 3 | 0 | 4 |
| 10 (pIVS-RE) | 4 | $5 \times 10^7$ (i.v.) | 100 | 100 | 60 | 74 | 48 | 75 | 4 | 1 | 4 |
| 10 (pIVS-RE) | 4 | $5 \times 10^8$ (i.v.) | 100 | 100 | 49 | 70 | 37 | 50 | 3 | 3 | 4 |

* Percentage of pigs that died due to infection or had to be killed for animal welfare reasons
¥ Percentage of pigs with specific symptoms
┆ Percentage of observations which matched the described criteria
‖ Ataxia, lameness of at least one joint and/or stiffness
¤ Inappetance and/or depression
à Percentage of observations for the experimental group of a body temperature of > 40° C.
£ Percentage of blood samples for the group in which the concentration of granulocytes was > $10^{10}$/liter

TABLE 4

*S. suis* genes selected in pigs.

| Clone | Sites of isolation | Insert (bp) | GC % | Data base homology (accession no.) | Function of homolog | % Identity |
|---|---|---|---|---|---|---|
| | | | | Putative virulence factors | | |
| ivs 31 (SEQ ID NO: 37) | CNS | 200 | 47 | *S. gordonii* FlpA (X65164) | fibronectin/fibrinogen binding | 70 |
| | | | | Regulatory functions | | |
| ivs 25 (SEQ ID NO: 34) | joint | 800 | 34 | *S. mutans* SapR (P72485) | response regulator protein | 49 |
| | | | | *S. aureus* AgrA (X52543) | response regulator protein | 51 |
| | | | | *S. suis* Iri 1, 6, 22 | | 100 |
| ivs 23, 24 (SEQ ID NO: 33) | other | 850 | 38 | *S. agalactiae* CpsY (CAB36982) | regulation capsule expression | 46 |
| | | | | *E. coli* OxyR (P11721) | oxidative stress regulator | 51 |
| | | | | *S. suis* Iri 24 | | 100 |

TABLE 4-continued

S. suis genes selected in pigs.

| Clone | Sites of isolation | Insert (bp) | GC % | Data base homology (accession no.) | Function of homolog | % Identity |
|---|---|---|---|---|---|---|
| ivs 16 (SEQ ID NO: 28) | CNS | 800 | 43 | S. epidermidis AltR (U71377) | putative transcriptional regulator | 26 |
| ivs 20 (SEQ ID NO: 32) | lung | 800 | 41 | L. lactis AldR (O34133) | putative regulator AldR | 64 |
| | | | | Metabolic functions | | |
| ivs 33 (SEQ ID NO: 39) | CNS | 570 | 36 | E. coli ThrC (P00934) | threonine synthase | 41 |
| ivs 5, 10, 12, 22 (SEQ ID NO: 42) | CNS, joint | 900 | 36 | S. gordonii Tdk (P47848) | thymidine kinase | 87 |
| ivs 18 (SEQ ID NO: 29) | lung | 730 | 32 | S. mutans NADH oxidase (JC4541) | NADH oxidase | 80 |
| | | | | Transporter functions | | |
| ivs 2, 4, 28 (SEQ ID NO: 31) | CNS, joint | 1350 | 51 | E. coli YoaE (P76262) | putative transport protein | 94 |
| | | | | S. suis iri 10, 20 | | 100 |
| ivs 3 (SEQ ID NO: 36) | joint | 1000 | 42 | S. mutans OrfU (AF267498) | putative ABC transporter (permease) | 33 |
| ivs 6, 7, 13, 14 (SEQ ID NO: 43) | CNS, joint | 1350 | 36 | B. subtilis Ylo D (O34328) | putative guanylate kinase | 50 |
| | | | | S. gordonii ComYa (U81957) | putative ABC transporter | 37 |
| | | | | V. cholera IviVI (Q56605) | putative ABC transporter | 47 |
| | | | | S. suis Iri 2 | | 100 |
| | | | | Transposases | | |
| ivs 8 (SEQ ID NO: 44) | CNS | 600 | 41 | S. pneumoniae transposase (Z86112) | transposase | 70 |
| ivs 1 (SEQ ID NO: 25) | joint | 1600 | 39 | C. perfringens (X71844) | putative transposase | 56 |
| | | | | Miscellaneous | | |
| ivs 32, 35 (SEQ ID NO: 38) | CNS | 500 | 38 | S. typhimurium FliF (P15928) | flagellar M-protein precursor | 36 |
| ivs 9, 17 (SEQ ID NO: 45) | joint, CNS | 800 | 36 | B. subtilis ComE ORF2 (P32393) | competence development | 37 |
| ivs 11 (SEQ ID NO: 26) | serosea | 800 | 44 | P. syringae TabA (P31851) | diaminopimelate decarboxylase/tabtoxin | 53 |
| | | | | Unknown | | |
| ivs 15 (SEQ ID NO: 27) | CNS | 750 | 42 | B. subtilis conserved hypothetical protein YdiB (D88802) | unknown | 43 |
| ivs 29 (SEQ ID NO: 35) | joint | 800 | 38 | S. salivarius hypothetical protein (AF130465) | unknown | 79 |
| ivs 34 (SEQ ID NO: 40) | CNS | 600 | 43 | B. subtilis conserved hypothetical protein YRRK (O34634) | unknown | 61 |
| ivs 36 (SEQ ID NO: 41) | joint | 830 | 42 | B. subtilis hypothetical protein YqeG (P54452) | unknown | 35 |
| ivs 19 (SEQ ID NO: 30) | lung | 950 | 34 | S. cristatus hypothetical protein (U96166) | unknown | 86 |

TABLE 5

Bacterial strains and plasmids.

| Strain/plasmid | Relevant Characteristics[a] | Source/reference |
|---|---|---|
| Strains | | |
| *E. coli* | | |
| XL2-Blue | recA1 endA1 gyrA96 thi-1 hsdR17 supE44 relA1 lac (F' proAB lacI$^q$ Z)M15 TN10 (Tet$^R$) amy Cm$^R$) | Stratagene |
| M15 | Nal$^S$ Str$^S$ Rif$^S$ Thi$^-$ Lac$^-$ Ara$^+$ Gal$^+$ Mtl$^-$ F$^-$ RecA$^+$ Uvr$^+$ Lon$^+$ | Qiagen |
| *S. suis* | | |
| 10 | Virulent serotype 2 strain | Vecht et al. (29) |
| 10ΔFBPS | Isogenic fbps mutant of strain 10 | This work |
| Plasmids | | |
| pGEM7Zf(+) | Replication functions pUC, Amp$^R$ | Promega Corp. |
| pKUN19 | Replication functions pUC, Amp$^R$ | Konings et al. (14) |

TABLE 5-continued

Bacterial strains and plasmids.

| Strain/plasmid | Relevant Characteristics[a] | Source/reference |
|---|---|---|
| pIC19R | Replication functions pUC, Amp[R] | Marsh et al. (16) |
| pDL282 | Replication functions of pBR322 and pVT736-1, Amp[R], Spc[R] | Sreenivasan et al. (25) |
| pIC-spc | pIC19R containing Spc[R] gene of pDL282 | Lab collection |
| pQE-30 | Replication functions pBR322, Amp[R], expression vector, 6x HIS tag | Qiagen |
| pQE-30-FBPS | pQE-30 containing the 1.8 kb fbps gene | This work |
| pREP4 | Replication functions pACYC, Kan[R], lacI gene | Qiagen |
| pE194 | Em[R] | Horinouchi and Weisblum (11) |
| pIVS-E | Replication functions of pWVO1, Spc[R], promoterless erm gene of pE194 | Smith et al. (20) |
| pIVS-31 | pIVS-E containing 200 bp showing homology to *Streptococcus gordonii* flpa | Smith et al. (20) |
| pFBPS7-46 | pGEM7Zf(+) containing EcoRI-EcoRI fragment of fbps | This work |
| pFBPS7-47 | pFBPS7-46 in which 382 bp SalI-SalI fragment is replaced by 1.2 kb Spc[R] from pIC-spc | This work |

[a]Tet[R] tetracycline resistant
Cm[R] chloramphenicol resistant
Amp[R] ampicillin resistant
Spc[R] spectinomycin resistant
Kan[R] kanamycin resistant
FBPS fibronectin binding protein *S. suis*

TABLE 6

Numbers of re-isolated wild-type (strain 10) and mutant (strain 10ΔFBPS) bacteria from organs of infected piglets (mean actual inoculation ratio 65% mutant strain).

| | Pig number | | | | | | | | | | | |
|---|---|---|---|---|---|---|---|---|---|---|---|---|
| | 4664 | | | 4665 | | | 4666 | | | 4667 | | |
| Organ | w.t.[a] | mut.[b] | perc.[c] mut. | w.t.[a] | mut.[b] | perc.[c] mut. | w.t.[a] | mut.[b] | perc.[c] mut. | w.t.[a] | mut.[b] | perc.[c] mut. |
| Tonsil | $1.77^e5$ | $3.29^e5$ | 65 | $4.35^e5$ | $2.42^e6$ | 85 | $5.34^e4$ | $8.73^e4$ | 61 | $7.94^e5$ | $3.96^e5$ | 33 |
| pus joint 1 | $6.75^e4$ | <10 | 0 | | | | $1.02^e2$ | $5.2^e2$ | 84 | | | |
| pus joint 2 | $5.15^e4$ | <10 | 0 | | | | | | | | | |
| CNS | | | | | | | | | | $1.88^e5$ | <10 | 0 |

CNS Central Nervous System
[a]number of wild-type bacteria found (cfu/ml)
[b]number of mutant bacteria found (cfu/ml)
[c]percentage of mutant bacteria calculated as follows: b/(a + b) * 100%
Only relevant organs are depicted.

REFERENCES

Arends, J. P. and H. C. Zanen. (1988). Meningitis caused by *Streptococcus suis* in humans. *Rev. Infect. Dis.* 10, 131-137.

Axelsson, L. and A. Holck. (1995). The genes involved in production of and immunity to sakacin A, a bacteriocin from *Lactobacillus sake* Lb706. *J. Bacteriol.* 177, 2125-2137.

Camacho, L. R., D. Ensergueix, E. Perez, B. Gicquel and C. Guilhot. (1999). Identification of a gene cluster of *Mycobacterium tuberculosis* by signature-tagged transposon mutagenesis. *Mol. Microbiol.* 34, 257-267.

Camilli, A. and J. J. Mekalanos. (1995). Use of recombinase gene fusions to identify *Vibrio cholerae* genes induced during infection. *Mol. Microbiol.* 18, 671-683.

Chiang, S. L. and J. J. Mekalanos. (1998). Use of signature-tagged transposon mutagenesis to identify *Vibrio cholerae* genes critical for colonization. *Mol. Microbiol.* 27, 797-805.

Clifton-Hadley, F. A. (1983). *Streptococcus suis* type 2 infections. *Br. Vet. J.* 139, 1-5.

Conner, C. P., D. M. Heithoff, S. M. Julio, R. L. Sinsheimer and M. J. Mahan. (1998). Differential patterns of acquired virulence genes distinguish *Salmonella* strains. *Proc. Natl. Acad. Sci. USA* 95, 4641-4645.

Coulter, S. N., W. R. Schwan, E. Y. W. Ng, M. H. Langhorne, H. D. Ritchie, S. Westbrock-Wadman, W. O. Hufnagle, K. R. Folger, A. S. Bayer and C. K. Stover. (1998). *Staphylococcus aureus* genetic loci impacting growth and survival in multiple infection environments. *Mol. Microbiol.* 30, 393-404.

Courtney, H. S., J. B. Dale, Y. Li and D. L. Hasty. (1994). Cloning, sequencing, and expression of a fibronectin/fibrinogen-binding protein from group A Streptococci. *Infect. Immun.* 62, 3937-3946.

Darwin, A. J. and V. L. Miller. (1999). Identification of *Yersinia enterocolitica* genes affecting survival in an animal host using signature-tagged transposon mutagenesis. *Mol. Microbiol.* 32, 51-62.

Demple, B. (1999). Radical ideas: genetic responses to oxidative stress. *Clin. Exp. Pharm. Phys.* 26, 64-68.

Edelstein, P. H., M. A. C. Edelstein, F. Higa and S. Falkow. (1999). Discovery of virulence genes of *Legionella pneumophila* by using signature tagged mutagenesis in a guinea pig pneumonia model. *Proc. Natl. Acad. Sci. USA* 96, 8190-8195.

Elliott, S. D. and J. Y. Tai. (1978). The type specific polysaccharide of *Streptococcus suis*. *J. Exp. Med.* 148, 1699-1704.

Fuller, T. E., R. J. Shea, B. J. Thacker and M. H. Mulks. (1999). Identification of in vivo induced genes in *Actinobacillus pleuropneumoniae*. *Microb. Path.* 27, 311-327.

Gottschalk, M., S. Lacouture and J. D. Dubreuil. (1995). Characterization of *Streptococcus suis* type 2 hemolysin. *Microbiology* 141, 189-195.

Hensel, M., J. E. Shea, C. Gleeson, M. D. Jones, E. Dalton and D. W. Holden. (1995). Simultaneous identification of bacterial virulence genes by negative selection. *Science* 269, 400-403.

Horinouchi, S. and B. Weisblum. (1982). Nucleotide sequence and functional map of pE194, a plasmid that specifies inducible resistance to macrolide, lincosamide and streptogramin type B antibiotics. *J. Bacteriol.* 150, 804-814.

Jacobs, A. A., P. L. W. Loeffen, A. J. G. van den Berg and P. K. Storm. (1994). Identification, purification and characterization of a thiol-activated hemolysin (suilysin) of *Streptococcus suis*. *Infect. Immun.* 62, 1742-1748.

Kolkman, M. A. B., W. Wakarchuk, P. J. M. Nuijten and B. A. M. van der Zeijst. (1997). Capsular polysaccharide synthesis in *Streptococcus pneumoniae* serotype 14: molecular analysis of the complete cps locus and identification of genes encoding glycosyltransferases required for the biosynthesis of the tetrasaccharide subunit. *Mol. Microbiol.* 26, 197-208.

Konings, R. N. H., E. J. M. Verhoeven and B. P. H. Peeters. (1987). pKUN vectors for the separate production of both DNA strands of recombinant plasmids. *Methods Enzymol.* 153, 12-34.

Koskiniemi, S., M. Sellin and M. Norgren. (1998). Identification of two genes, cpsX and cpsY, with putative regulatory function on capsule expression in group B Streptococci. *FEMS Immun. Med. Microbiol.* 21, 159-168.

Litwin, C. M. and S. B. Calderwood. (1993). Role of iron regulation of virulence genes. *Clin. Microbiol. Rev.* 6, 137-149.

Lowe, A. M., D. T. Beattie and R. L. Deresiewics. (1998). Identification of novel staphylococcal virulence genes by in vivo expression technology. *Mol. Microbiol.* 27, 967-976.

Mahan, M. J., J. M. Slauch and J. J. Mekalanos. (1993). Selection of bacterial virulence genes that are specifically induced in host tissues. *Science* 259, 686-688.

Mahan, M. J., T. W. Tobias, J. M. Slauch, P. C. Hanna, R. J. Collier and J. J. Mekalanos. (1995). Antibiotic-based selection for bacterial genes that are specifically induced during infection of a host. *Proc. Natl. Acad. Sci. USA* 92, 669-673.

Martinez, J. L., A. Delgado-Iribarren and F. Basquero. (1990). Mechanisms of iron acquisition and bacterial virulence. *FEMS Microbiol.* 75, 45-56.

Mei, J-M., F. Nourbakhsh, C. W. Ford and D. W. Holden. (1997). Identification of *Staphylococcus aureus* virulence genes in a murine model of bacteremia using signature-tagged mutagenesis. *Mol. Microbiol.* 26, 399-407.

Miller, J. (1972). *Experiments in Molecular Genetics*. Cold Spring Harbor, N.Y.: Cold Spring Harbor Laboratory.

Niven, D. F., A. Ekins and A. A.-W Al-Samaurai. (1999). Effects of iron and manganese availability on growth and production of superoxide dismutase by *Streptococcus suis*. *Can. J. Microbiol.* 45, 1027-1032.

Payne, S. M. (1993). Iron acquisition in microbial pathogenesis. *Trends Microbiol.* 1, 66-69.

Polissi, A., A. Pontiggia, G. Feger, M. Altieri, H. Mottl, L. Ferrari and D. Simon. (1998). Large-scale identification of virulence genes from *Streptococcus pneumoniae*. *Infect. Immun.* 66, 5620-5629.

Projan, S. J. and R. P. Novick. (1997). The molecular basis of pathogenicity. *The Staphylococci in Human Disease*, pp 55-81. Edited by K. B. Crossley and G. L. Archer. Churchill Livingstone, NY.

Quessy, S., J. D. Dubreuil, M. Jacques, F. Malouin and R. Higgins. (1994). Increase in capsular material thickness following in vivo growth of virulent *Streptococcus suis* serotype 2 strains. *FEMS Microbiol. Lett.* 115, 19-26.

Sambrook, J., E. F. Fritsch and T. Maniatis. (1989). *Molecular Cloning: a Laboratory Manual*, 2nd edn. Cold Spring Harbor, N.Y.: Cold Spring Harbor Laboratory.

Segers, R. P. A. M., T. Kenter, L. A. M. de Haan and A. A. C. Jacobs. (1998). Characterization of the gene encoding suilysin from *Streptococcus suis* and expression in field strains. *FEMS Microbiol. Lett.* 167, 255-261.

Serhir, B., D. Dugourd, M. Jacques, R. Higgins and J. Harel. (1997). Cloning and characterization of a dextranase gene (dexS) from *Streptococcus suis*. *Gene* 19, 257-261.

Smith, H. E., U. Vecht, A. L. J. Gielkens and M. A. Smits. (1992). Cloning and nucleotide sequence of the gene encoding the 136-kilodalton surface protein (muramidase-released protein) of *Streptococcus suis* type 2. *Infect. Immun.* 60, 2361-2367.

Smith, H. E., F. H. Reek, U. Vecht, A. L. J. Gielkens and M. A. Smits. (1993). Repeats in an extracellular protein of weakly pathogenic strains of *Streptococcus suis* type 2 are absent in pathogenic strains. *Infect. Immun.* 61, 3318-3326.

Smith, H. E., H. J. Wisselink, U. Vecht, A. L. J. Gielkens and M. A. Smits. (1995). High-efficiency transformation and gene inactivation in *Streptococcus suis* type 2. *Microbiol.* 141, 181-188.

Smith, H. E., U. Vecht, H. J. Wisselink, N. Stockhofe-Zurwieden, Y. Biermann and M. A. Smits. (1996). Mutants of *Streptococcus suis* types 1 and 2 impaired in expression of muranidase-released protein and extracellular protein induce disease in newborn germ-free pigs. *Infect. Immun.* 64, 4409-4412.

Smith, H. E., M. Damman, J. van der Velde, F. Wagenaar, H. J. Wisselink, N. Stockhofe-Zurwieden and M. A. Smits. (1999). Identification and characterization of the cps locus of *Streptococcus suis* serotype 2: the capsule protects against phagocytosis and is an important virulence factor. *Infect. Immun.* 67, 1750-1756.

Stockhofe-Zurwieden, N., U. Vecht, H. J. Wisselink, H. van Lieshout and H. E. Smith. (1996). Comparative studies on the pathogenicity of different *Streptococcus suis* serotype 1 strains. In *Proceedings of the 14th International Pig Veterinary Society Congress*, pp 299. Edited by P. G. Monetti and G. Vignola. Bologna, Italy.

Van der Vossen, J. M. B. M., D. van der Lelie and G. Venema. (1987). Isolation and characterization of *Lactococcus lactis* subsp. cremoris Wg2-specific promoters. *Appl. Environ. Microbiol.* 52, 2452-2457.

Vecht, U., L. A. M. G. van Leengoed and E. R. M. Verheyden. (1985). *Streptococcus suis* infections in pigs in The Netherlands (part one). *Vet. Quart.* 7: 315-321.

Vecht, U., J. P. Arends, E. J. van der Molen and L. A. M. G. van Leengoed. (1989). Difference in virulence between two strains of *Streptococcus suis* type 2 after experimentally induced infection of newborn germ-free pigs. *Am. J. Vet. Res.* 50, 1037-1043.

Vecht, U., H. J. Wisselink, M. L. Jellema and H. E. Smith. (1991). Identification of two proteins associated with virulence of *Streptococcus suis* type 2. *Infect. Immun.* 59, 3156-3162.

Vecht, U., H. J. Wisselink, J. E. van Dijk and H. E. Smith. (1992). Virulence of *Streptococcus suis* type 2 strains in newborn germ-free pigs depends on phenotype. *Infect. Immun.* 60, 550-556.

Vecht, U., N. Stockhofe-Zurwieden, B. J. Tetenburg, H. J. Wisselink and H. E. Smith. (1997). Virulence of *Streptococcus suis* type 2 for mice and pigs appeared host-specific. *Vet. Microbiol.* 58, 53-60.

Wang, J., A. Mushegian, S. Lory and S. Jin. (1996). Large-scale isolation of candidate virulence genes of *Pseudomonas aeruginosa* by in vivo selection. *Proc. Natl. Acad. Sci. USA* 93, 10434-10439.

Yamashita, Y., Y. Shibata, Y. Nakano, H. Tsuda, N. Kido, M. Ohta and T. Koga. (1999). A novel gene required for rhamnose-glucose polysaccharide synthesis in *Streptococcus mutans*. *J. Bacteriol.* 181, 6556-6559.

Young, G. M. and V. L. Miller. (1997). Identification of novel chromosomal loci affecting *Yersinia enterocolitica* pathogenesis. *Mol. Microbiol.* 25, 319-328.

Zhao, H., X. Li, D. E. Johnson and H. L. T. Mobley. (1999). Identification of protease and rpoN-associated genes of uropathogenic *Proteus mirabilis* by negative selection in a mouse model of ascending urinary tract infection. *Microbiol.* 145, 185-195.

OTHER REFERENCES

1. Allgaier A. R. G., H. J. Wisselink, H. E. Smith, and P. Valentin-Weigand. 2001. Relatedness of *Streptococcus suis* isolates of various serotypes and clinical backgrounds as evaluated by macrorestriction analysis and expression of potential virulence traits. *J. Clin. Microbiol.* 39:445-453.
2. Allen, A. G., S. Bolitho, H. Lindsay, S. Khan, C. Bryant, P. Norton, P. Ward, J. Leigh, J. Morgan, H. Riches, S. Eastty, D. Maskell. 2001. Generation and characterization of a defined mutant of *Streptococcus suis* lacking suilysin. *Infect. Immun.* 69:2732-2735.
3. Arends, J. P., and H. C. Zanen. 1988. Meningitis caused by *Streptococcus suis* in humans. *Rev. Infect. Dis.* 10:131-137.
4. Charland, N., V. Nizet, C. Rubens, K. Kim, S. Lacouture, and M. Gottschalk. 2000. *Streptococcus suis* interactions with human brain microvascular endothelial cells. *Infect. Immun.* 68:637-643.
5. Chia, J. S., C. Y. Yeh, and J. Y. Chen. 2000. Identification of a fibronectin binding protein from *Streptococcus mutans*. *Infect. Immun.* 68:1864-1870.
6. Clifton-Hadley, F. A. 1983. *Streptococcus suis* type 2 infections. *Br. Vet. J.* 139:1-5.
7. Courtney, H. S., J. B. Dale, and D. L. Hasty. 1996. Differential effects of the Streptococcal fibronectin-binding protein, FBP54, on adhesion of group A Streptococci to human buccal cells and Hep-2 tissue culture cells. *Infect. Immun.* 64:2415-2419.
8. Courtney, H. S., Y. Li, J. B. Dale, and D. L. Hasty. 1994. Cloning, sequencing, and expression of a fibronectin/fibrinogen-binding protein from group A Streptococci. *Infect. Immun.* 62:3937-3946.
9. Fuller, T. E., S. Martin, J. F. Teel, G. R. Alaniz, M. J. Kennedy, and D. E. Lowery. 2000. Identification of *Actinobacillus pleuropneumoniae* virulence genes using signature-tagged mutagenesis in a swine infection model. *Microb. Pathog.* 29:39-51.
10. Greene, C., D. McDevitt, P. Francois, P. Vaudaux, and T. J. Foster. 1995. Adhesion properties of mutants of *Staphylococcus aureus* defective in fibronectin-binding proteins and studies on the expression of fnb genes. *Mol. Microbiol.* 17:1065-1076.
11. Horinouchi, S., and B. Weisblum. 1982. Nucleotide sequence and functional map of pE194, a plasmid that specifies inducible resistance to macrolide, lincosamide and streptogramin type B antibiotics. *J. Bacteriol.* 150:804-815.
12. Joh, D., E. R. W. Wann, B. Kreikemeyer, P. Speziale, and M. Höök. 1999. Role of fibronectin-binding MSCRAMMS in bacterial adherence and entry into mammalian cells. *Matrix Biol.* 18:211-223.
13. Kawabata, S., E. Kunitomo, Y. Terao, I. Nagakawa, K. Kiruchi, K.-I. Totsuka, and S. Hamada. 2001. Systemic and mucosal immunizations with fibronectin-binding protein FBP54 induce protective immune responses against *Streptococcus pyogenes* challenge in mice. *Infect. Immun.* 69:924-930.
14. Konings, R. N. H., E. J. M. Verhoeven, and B. P. H. Peeters. 1987. pKUN vectors for the separate production of both DNA strands of recombinant plasmids. *Methods Enzymol.* 153:12-34.
15. Mahan, M. J., J. M. Slauch, and J. J. Mekalanos. 1993. Selection of bacterial virulence genes that are specifically induced in host tissues. *Science* 259:686-688.
16. Marsh, J. L., M. Erfle, and E. J. Wykes. 1984. The pIC plasmid and phage vectors with versatile cloning sites for recombinant selection by insertional inactivation. *Gene* 32:481-485.
17. Miller, J. 1972. Experiments in molecular genetics. Cold Spring Harbor Laboratory. Cold Spring-Harbor, N.Y.
18. Peacock, S. J., T. J. Foster, B. J. Cameron, and A. R. Berendt. 1999. Bacterial fibronectin-binding proteins and endothelial cell surface fibronectin mediate adherence of *Staphylococcus aureus* to resting human endothelial cells. *Microbiology* 145:3477-3486.
19. Sambrook, J., E. F. Fritsch, and T. Maniatis. 1989. Molecular cloning: a laboratory manual, 2nd ed. Cold Spring Harbor Laboratory Press, Cold Spring Harbor. N.Y.
20. Smith, H. E., H. Buijs, R. de Vries, H. J. Wisselink, N. Stockhofe-Zurwieden, and M. A. Smits. 2001. Environmentally regulated genes of *Streptococcus suis*: identification by the use of iron-restricted conditions in vitro and by experimental infection of piglets. *Microbiol.* 147:271-280.
21. Smith, H. E., H. Buijs, H. J. Wisselink, N. Stockhofe-Zurwieden, and M. A. Smits. 2001. Selection of virulence-associated determinants of *Streptococcus suis* serotype 2 by in vivo complementation. *Infect. Immun.* 69:1961-1966.
22. Smith, H. E., M. Damman, J. van der Velde, F. Wagenaar, H. J. Wisselink, N. Stockhofe-Zurwieden, and M. A. Smits. 1999. Identification and characterization of the cps locus of *Streptococcus suis* serotype 2: the capsule protects against phagocytosis and is an important virulence factor. *Infect. Immun.* 60:1750-1756.
23. Smith, H. E., U. Vecht, H. J. Wisselink, N. Stockhofe-Zurwieden, Y. Biermann, and M. A. Smits. 1996. Mutants of *Streptococcus suis* types 1 and 2 impaired in expression of murimidase-released protein and extracellular protein induce disease in newborn germ-free pigs. *Infect. Immun.* 64:4409-4412.
24. Smith, H. E., H. J. Wisselink, U. Vecht, A. L. J. Gielkens, and M. A. Smits. 1995. High-efficiency transformation and gene inactivation in *Streptococcus suis* type 2. *Microbiology* 141:181-188.

25. Sreenivasan, P. K., D. L. LeBlanc, L. N. Lee, and P. Fives-Taylor. 1991. Transformation of *Actinobacillus actinomycetemcomitans* by electroporation, utilizing constructed shuttle plasmids. *Infect. Immun.* 59:4621-4627.
26. Staats, J. J., I. Feder, O. Okwumabua, and M. M. Cheganppa. 1995. *Streptococcus suis*: past and present. *Vet. Res. Comm.* 21:381-407.
27. Vecht, U., J. P. Arends, E. J. van der Molen, and L. A. M. G. van Leengoed. 1989. Differences in virulence between two strains of *Streptococcus suis* type 2 after experimentally induced infection of newborn germ-free pigs. *Am. J. Vet. Res.* 50:1037-1043.
28. Vecht, U., L. A. M. G. van Leengoed, and E. R. M. Verheyen. 1985. *Streptococcus suis* infections in pigs in The Netherlands (part I). *Vet. Q.* 7:315-321.
29. Vecht, U., H. J. Wisselink, J. E. van Dijk, and H. E. Smith. 1992. Virulence of *Streptococcus suis* type 2 strains in newborn germ-free pigs depend on phenotype. *Infect. Immun.* 60:550-556.
30. Vecht, U., H. J. Wisselink, M. L. Jellema, and H. E. Smith. 1991. Identification of two proteins associated with virulence of *Streptococcus suis* type 2. *Infect. Immun.* 59:3156-3162.

What is claimed is:

1. An isolated or recombinant nucleic acid molecule comprising:

a first nucleotide sequence of *Streptococcus suis* origin wherein the first nucleotide sequence comprises a contiguous sequence which hybridizes to the full length of nucleotides 89-263 of the nucleotide sequence of SEQ ID NO:37 at 65° C. in a buffer having 0.5 M sodium phosphate, 1 mM EDTA, and 7% sodium dodecyl sulphate at a pH of 7.2, wherein the first nucleic acid molecule remains hybridized to the nucleotide sequence of SEQ ID NO:37 after washing twice with a buffer containing 40 mM sodium phosphate (pH 7.2), 1 mM EDTA and 5% sodium dodecyl sulphate for 30 minutes at 65° C. and;

washing twice with a buffer containing 40 mM sodium phosphate (pH 7.2), 1 mM EDTA and 1% sodium dodecyl sulphate for 30 minutes at 65° C.

2. A vector comprising the isolated or recombinant nucleic acid molecule of claim 1.

3. A host cell comprising the isolated or recombinant nucleic acid molecule of claim 1.

4. The host cell of claim 3, wherein the host cell is of a *Streptococcus* origin.

5. A composition comprising the isolated or recombinant nucleic acid molecule of claim 1.

6. A process for modulating virulence of a *Streptococcus* comprising: providing a *Streptococcus* species having a genomic fragment capable of hybridizing to the isolated or recombinant nucleic acid molecule of claim 1; modifying the genomic fragment of the *Streptococcus* species, wherein modifying the genomic fragment comprises functionally deleting at least part of the genomic fragment; and generating a *Streptococcus* clone having the modified genomic fragment.

7. A clone of a *Streptococcus*, obtained by the process according to claim 1.

8. A process for assaying virulence of a *Streptococcus* comprising: providing a *Streptococcus* species; providing genomic DNA of said *Streptococcus* species; determining whether at least part of the genomic DNA is capable of hybridizing to the isolated or recombinant nucleic acid molecule of claim 1; wherein the capability of at least part of the genomic fragment to hybridize to the isolated or recombinant nucleic acid molecule of claim 1 is indicative for the virulence of the *Streptococcus*.

9. An isolated or recombinant nucleic acid molecule comprising a nucleotide sequence of *Streptococcus suis* origin comprising nucleotides 89-263 of SEQ ID NO:37.

* * * * *

SEQUENCE LISTING

```
<160> NUMBER OF SEQ ID NOS: 47

<210> SEQ ID NO 1
<211> LENGTH: 6
<212> TYPE: PRT
<213> ORGANISM: Artificial Sequence
<220> FEATURE:
<223> OTHER INFORMATION: Cell wall signalling sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1

Leu Pro Xaa Thr Gly Glu
1               5

<210> SEQ ID NO 2
<211> LENGTH: 30
<212> TYPE: DNA
<213> ORGANISM: artificial sequence
<220> FEATURE:
<223> OTHER INFORMATION: PCR primer containing NsiI and SacI restriction
      sites at the 5' end

<400> SEQUENCE: 2
tgcatgcatg gatccatcga ttttcgttcg                                        30

<210> SEQ ID NO 3
<211> LENGTH: 30
<212> TYPE: DNA
<213> ORGANISM: artificial sequence
<220> FEATURE:
<223> OTHER INFORMATION: PCR primer containing NsiI and SacI restriction
      sites at the 5'-end

<400> SEQUENCE: 3
cgagctcggt acctgattac caattagaat                                        30

<210> SEQ ID NO 4
<211> LENGTH: 30
<212> TYPE: DNA
<213> ORGANISM: artificial sequence
<220> FEATURE:
<223> OTHER INFORMATION: PCR primer containing SalI and HindIII
      restriction sites at the 5'-end

<400> SEQUENCE: 4
gggtcgaccc tataaccaaa ttaaagaggg                                        30

<210> SEQ ID NO 5
<211> LENGTH: 32
<212> TYPE: DNA
```

```
<213> ORGANISM: artificial sequence
<220> FEATURE:
<223> OTHER INFORMATION: PCR primer containing SalI and HindIII
      restriction sites at the 5'-end

<400> SEQUENCE: 5
cccaagcttg ggcagtttat gcatcccttaac                                    32

<210> SEQ ID NO 6
<211> LENGTH: 34
<212> TYPE: DNA
<213> ORGANISM: artificial sequence
<220> FEATURE:
<223> OTHER INFORMATION: PCR primer containing EcoRI and SalI
      restriction sites at the 5'-end

<400> SEQUENCE: 6
cccaagcttg ggaattcata atgttttttt gagg                                 34

<210> SEQ ID NO 7
<211> LENGTH: 30
<212> TYPE: DNA
<213> ORGANISM: artificial sequence
<220> FEATURE:
<223> OTHER INFORMATION: PCR primer containing EcoRI and SalI
      restriction sites at the 5'-end

<400> SEQUENCE: 7
gcgtcgacat ctacgcataa aaaatccccc                                      30

<210> SEQ ID NO 8
<211> LENGTH: 335
<212> TYPE: DNA
<213> ORGANISM: Streptococcus suis
<220> FEATURE:
<223> OTHER INFORMATION: iri 1, 6, 22
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (334)..(334)
<223> OTHER INFORMATION: n is a, c, g, or t

<400> SEQUENCE: 8
gaaacgtcag taaggtataa attcctagaa gttnttggta aaccaaatca atnattggaa      60
tcaattgggg aagcagggaa tcatcaattt ttcttttag atattgaaat aaaaggagaa     120
gaaaagaaag gaatggaaat cgctaaagaa atccgggctc gagatcctta tgctgctatt    180
gtctttgtaa caactcactc agaattnatg ccagtaacat atcgttatca ggtttctgct    240
ttagatttta tagataaagg cctggaggat cgtgactttc aaaaggcagt atcagangtc    300
ttagtgcatg cttttgaaaa tatcgatcat actnt                               335

<210> SEQ ID NO 9
<211> LENGTH: 347
```

```
<212> TYPE: DNA
<213> ORGANISM: Streptococcus suis
<220> FEATURE:
<223> OTHER INFORMATION: iri 10, 20
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (346)..(346)
<223> OTHER INFORMATION: n is a, c, g, or t

<400> SEQUENCE: 9
gntnggcggt tttccagccc gttnatgcag ttnggttgtt gctnngaaca gcaagaatat      60 ccccncngaac aacataatca ggtcgngtcc ggagaaggag aaatcccatg acggtaaatn    120
gcggtttggt cagngtgacc atccatgaaa tcagcgacag cagccccaga cgcataatca    180
gcgccagtga taacccagc aaacgcgctt tatcgngttg ttttggcggc agtttgtcag    240
caagaatggc gatgaagacc aggttataga tacccagcac aatttcgaga acaaccagcg    300
tgagtagccc cgcccaaatt gagggtcca ttaagncnta cgaaant                    347

<210> SEQ ID NO 10
<211> LENGTH: 339
<212> TYPE: DNA
<213> ORGANISM: Streptococcus suis
<220> FEATURE:
<223> OTHER INFORMATION: iri 11
<220> FEATURE:
<221> NAME/KEY: misc_feature
```

```
<222> LOCATION: (9)..(9)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t

<400> SEQUENCE: 10
ttcatcctng tcgagngggg aaatggggca cagttgtttt ccaattgata gaattttaa      60 gaacctatat atanaaacat ggataggttg tttaatattt tttnacacaa gatattgatt    120
tttgttttgt gaagtgctac actaatagaa gtgaagaatt ttggaggttt gtcagatgaa    180
tgtgcaagaa aatgtcttac cgagtataga attattggtt ttgaaacgtg atggacggac    240
agtatccttt gaccangata agatttttn tgctcttcag cgggcaaacc aagaattaga    300
acatcctgtt tcagnggcag gtttaaaaat tgtattaga                          339

<210> SEQ ID NO 11
<211> LENGTH: 270
<212> TYPE: DNA
<213> ORGANISM: Streptococcus suis
<220> FEATURE:
<223> OTHER INFORMATION: iri 13, 15, 27
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
```

```
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (266)..(266)
<223> OTHER INFORMATION: n is a, c, g, or t

<400> SEQUENCE: 11
ggaggnggtt anacnggcat ttgcagatgc cgaatttatc taatgatttt gtagaagagt      60
ggtngcatng aacaaccctc tttatcntta agaaaatgnt aggatagtcg gtcaatctan     120
gctatactag aaacgttatt aagtcccgaa aaggtagttt atagactagt taatatttgc     180
agaaacactt gnaacacaat taaagaaact ggtantattg aatagtaagc gtaaaaactt     240
tactacactt cagtcactat tttacntcaa                                      270

<210> SEQ ID NO 12
<211> LENGTH: 288
<212> TYPE: DNA
<213> ORGANISM: Streptococcus suis
<220> FEATURE:
<223> OTHER INFORMATION: iri 14
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (224)..(224)
<223> OTHER INFORMATION: n is a, c, g, or t

<400> SEQUENCE: 12
tattnntagt gtactataga aaaaactaac ntaccacaan acgtgatagg ttagttaant      60
taatgacatt gggctntttg cccagcntct tttttnttat attagacagt atgtaggagg     120
tggntangtt agaaaattgg ttaaacacca aacaaggtca ggtgtttcat tacaagatgg     180
```

```
aaaagattga gtatgcccta gaactgctag ggaatcccca gttngcagtt ccggtcattc    240
atgtcgctgg aactaatggc aagggatcga ccattgcctt tatgcgca                 288
```

<210> SEQ ID NO 13
<211> LENGTH: 342
<212> TYPE: DNA
<213> ORGANISM: Streptococcus suis
<220> FEATURE:
<223> OTHER INFORMATION: iri 16
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t
<220> FEATURE:
<221> NAME/KEY: misc_feature
<222> LOCATION: (338)..(339)
<223> OTHER INFORMATION: n is a, c, g, or t

<400> SEQUENCE: 13

```
gtacggcaac cggaagataa caagggatnt ggcngcagtt ggcagntcaa atcggcattc    60
cttagtantc tgtcaacttt gaaaagagt actgggaccg cgtatttgag tacttttag    120 cagagtatcg ggntggtcgc acgcccnatc cagatgtcan gtgtaacaag ganatcaagt  180
```

-continued

```
tcaaggctttt nttggantac gntatgaact tgggtgcgga ctatgtggcg acagggcact      240
acgctcaggt nacccgcgac gangacggca ccgttcatat gctgcgtggg gcagataatg      300
gtaaggacca gacctatttc cncagccaac tctcacgnna ac                        342
```

<210> SEQ ID NO 14
<211> LENGTH: 340
<212> TYPE: DNA
<213> ORGANISM: Streptococcus suis
<220> FEATURE:
<223> OTHER INFORMATION: iri 18
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (112)..(113)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t

<400> SEQUENCE: 14

```
ctgtctaacc accctaacat ngcatantcc tccttttta tctatttat caaaaaatcg       60 gngcttttct accatttgtc aagttcatca aggtatttga cgaaaaatan tnngtgtctc      120
gtcatccaaa taaggaaatt gttttatttt ggactaaagt tacgtgtaaa aagngcatac     180 aaaccaaca ccttntgttg naatttttg ataaggtgtt acaatgatag agcataaaca       240
```

```
gttttaccga ttttgggtng aagcgtaatc gtnaaatttg ttatgcntaa tgaggtaata    300
cattgtccga atgagacgat gtatggaggc gatcgnangn                          340
```

<210> SEQ ID NO 15
<211> LENGTH: 355
<212> TYPE: DNA
<213> ORGANISM: Streptococcus suis
<220> FEATURE:
<223> OTHER INFORMATION: iri 2
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t

<400> SEQUENCE: 15

```
anccttctcnn ggcccnatgg atgtttcgng gagaaaattg gaaaaataat cggattatc    60 cagggaaatn tcaaaatcac agttatccgt gaaacaagag caacngangt tgcnaagtaa   120
atgtagaaga gtccgaaggg ctcttttttnt actggctcaa agttcgttan gggttgggaa   180
tagaaaatag aaaatatttt aatcgtattt aaaagcagtt gaaattcatg ctaaattttg   240
ttacactaga atgaaagatt taaaaggaga tatcatgaaa gagcgaggct tactcatngt   300
``` ctttctggt ccatctggtg cnggaaaagg aacagttcga aaggnaattt ntgaa    355

```
<210> SEQ ID NO 16
<211> LENGTH: 337
<212> TYPE: DNA
<213> ORGANISM: Streptococcus suis
<220> FEATURE:
<223> OTHER INFORMATION: iri 23
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (335)..(337)
<223> OTHER INFORMATION: n is a, c, g, or t

<400> SEQUENCE: 16
```
gntctngtag tagataagat tgaaacgcca aattcntcgt aacaaaacca agattgaacg    60
aaagcntcgt caaaaagtgg caactggtca agtctttaca gatgaacttg ttgngcaaac    120
aggcgaggaa gtaaaagtgg ttcgtactaa gcaagtagac ttgaaaccaa tggatatgga    180
agaagcagtc ctccaattgg agttgctcgg acatgatttc tttatctata cagatgctaa    240
tgacggtaca acaaatgtat tgtatagacg cgaagatgga gatttgggtc ttctagagnt    300
acgtcaataa agataataaa acagcncnan cgnannn    337

```
<210> SEQ ID NO 17
<211> LENGTH: 350
<212> TYPE: DNA
<213> ORGANISM: Streptococcus suis
<220> FEATURE:
<223> OTHER INFORMATION: iri 24
<220> FEATURE:
<221> NAME/KEY: misc_feature
<222> LOCATION: (24)..(24)
<223> OTHER INFORMATION: n is a, c, g, or t
```

```
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t

<400> SEQUENCE: 17
agaagagaaa tgggggaacc tggnagttct acaagaaatt agttttgaag aacaggacgg    60
ggctagtcta tttgcgaaaa cgcaagagtt cagcaaattc ttgcttttt tgatataatg   120 gtagaagcag ttttaagagg tatccaggta tgaatattca acaattacgc tacgttgtag   180
ccattgcaaa cagtggtaca tttcgagagg cggctgagaa aatgtangtg tcccagccta   240
gntngtccat ttccattcgt gatttggaaa aagagttagg ttttcaaatt tttngccgaa   300
ctagttcagg aacttttttg acacaaaaag ggatggnact cacggagata              350

<210> SEQ ID NO 18
<211> LENGTH: 333
<212> TYPE: DNA
<213> ORGANISM: Streptococcus suis
<220> FEATURE:
<223> OTHER INFORMATION: iri 29
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t

<400> SEQUENCE: 18
gcgtatgggg gaaattgccc aagatgttan ccggtgacaa aatcacagat gcagcccgta    60
atcangcaaa agaattagta gaaaaaggtt nggcgactag ccttttttgct catgtccaaa   120 gtttattttt tagttaaaat ttgttataat agatggcaaa attgaagaga attgtaggnt   180
gaaatatgtc aaagattaag attgttacgg attcaagtac gactatcgaa cccagtttgg   240
```

```
tcgaagaatt gaatataaca gttgttccnt tatctgtaat ggttgacgga gtcgtatact    300
ctgacaacga tttaaaagaa ggcgaantcn tag                                 333
```

<210> SEQ ID NO 19
<211> LENGTH: 341
<212> TYPE: DNA
<213> ORGANISM: Streptococcus suis
<220> FEATURE:
<223> OTHER INFORMATION: iri 3
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t

<400> SEQUENCE: 19

```
aggntgctan gaaaaaattg gctcacaaat catttctttt anttgacgat tgcctttctt    60
tngatttngg tgatttactt tagtggaata gataaacgtt ggattatttt ggcaagtttt   120
cttnacttca ttccatcgca gattttatac cgtcgtcgcc taagagagcg actccaagaa   180
gaccagccca agnaggcngg ttttttgatg tgtaaattgg actacaattc tttattaact   240
gtgctataat agttttttgca gaaaagtaaa gacggnggct ctaatttctg aaaggtaggt   300
ggtgtctatg ggcaaatcat cnaaatctna cagaaaggag n                        341
```

<210> SEQ ID NO 20
<211> LENGTH: 264
<212> TYPE: DNA
<213> ORGANISM: Streptococcus suis

```
<220> FEATURE:
<223> OTHER INFORMATION: iri 32
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t

<400> SEQUENCE: 20
gaatcgaatt ggagntcgcc cctcaaacgg ctggcatatc ttttcaatcc ttatctntna     60
gtcgcaagcg acaagganta gggatnatat aatctcctga gaatactgga ctcactgagt    120
ctggtatttt cattttatgc tataatggtt tcatgacaaa tcgaattta gatatggaac    180 aaatgcagga cgaggaatat gtcgngcgta ccctgcgtcc ncagaaatta aacgaataca    240
tcggtcagga caaggttaag gacc                                           264

<210> SEQ ID NO 21
<211> LENGTH: 338
<212> TYPE: DNA
<213> ORGANISM: Streptococcus suis
<220> FEATURE:
<223> OTHER INFORMATION: iri 34
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (304)..(304)
<223> OTHER INFORMATION: n is a, c, g, or t
<220> FEATURE:
<221> NAME/KEY: misc_feature
```

```
<222> LOCATION: (307)..(307)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t

<400> SEQUENCE: 21
acagtagcct atgaantctt ggaagnaagc gggaagaagc aaaccattag tttcgaccaa      60
attttagttc ccataggagg aggtggtctg gttgcaggcg tttcggccta tntgaaagaa     120
catgcacctg aaattangat tgttggtgtt gaagcaagtg gggcacggtc aatgaaagcg     180
gctttngata aaggtcgtcc ggttnaatta gaccaaattg ataaatttgc tgacggtatt     240
gcggtacaga aagtcggtaa gtcgacctac gaagtggctc ggaaatacgt agatcgcctg     300
attngtntgg atgaagggtg gatttccggg antatttt                             338

<210> SEQ ID NO 22
<211> LENGTH: 351
<212> TYPE: DNA
<213> ORGANISM: Streptococcus suis
<220> FEATURE:
<223> OTHER INFORMATION: iri 4
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (308)..(308)
<223> OTHER INFORMATION: n is a, c, g, or t

<400> SEQUENCE: 22
aaaatggcag gggggaccca agggaantct tttctgatat caaggacaa cctggtcagt      60
```

```
cagntggntc aantacaagc cttaccactn gaacaaatan tcgaaaaccg ttatcaacgc      120
tttagaaaat antaggaaga cctagnattt ttttgataga tttgatacaa tggataaaat      180
aatttcagga ggttttccat gttagtaaaa gcagatctat caaacgcagn agaattgcta      240
cntattcagc nccgagcatt tgcggcttta tataaaacct atcaggacca gtacaaccct      300
gccattgnaa ctatggacta tttccaatca cgctttgcac gaccaaattg t              351
```

<210> SEQ ID NO 23
<211> LENGTH: 362
<212> TYPE: DNA
<213> ORGANISM: Streptococcus suis
<220> FEATURE:
<223> OTHER INFORMATION: iri 7
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t

<400> SEQUENCE: 23

```
gaaattgatg ggcatctttg gtattaatag gaactccatg gctcaatctt cttcggttta      60
ttggtaatag tagttaccgt cangaanaaa tcgcaaagta taaaaagtgc tgtgaagaga     120 aaaaagaaa ataagaatct ttctaaacaa gataagagcc gtcaggctct tttttngata     180
taatatagtg gatatggtta attaaaattg tcagaaaaga ctattttana gattaacact     240
ctctgaaaat cntcattaac aagaaaagag gcngggctca agccccgcat cacntctcaa     300
agttagcgtc aacatctcag cgcagtagtg gtngattggg tttaacagtc cagtggagtg     360
tc                                                                   362
```

<210> SEQ ID NO 24
<211> LENGTH: 362
<212> TYPE: DNA
<213> ORGANISM: Streptococcus suis
<220> FEATURE:
<223> OTHER INFORMATION: iri 8, 26
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature

```
<222> LOCATION: (61)..(61)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t

<400> SEQUENCE: 24
ttcggaatcc ttctntctcc attggaacag ggatacaaag ggacgttaag gaaatccgta      60
ngaaaatagg aaattgacgc agtgtgctan acacacaggg aagtttatct ttttccacta     120
ggattttagt ccgtgttcaa ctaagatacg agatatgttc tggtttacca gaaatttcng     180
nagaaaatta ggagactgac gctgagtgtt aacactcaag gaaggctatc tattttttcta    240 agaaattaat ctcgagttca atttcttntg attagtaaat aaatgaattg tatctatttt    300
ttggggtatc gccaagcggt aaggcaaggg actttgactc cctcatgcgc cggttngcat    360
cc                                                                   362

<210> SEQ ID NO 25
<211> LENGTH: 405
<212> TYPE: DNA
<213> ORGANISM: Streptococcus suis
<220> FEATURE:
<223> OTHER INFORMATION: ivs 1

<400> SEQUENCE: 25
aatgatgttt gataaacacg ccaatctcaa atacaaattt ggtaatcgtc atttctgggc      60
agagggatat tatgtaagta cggttggact aaatgaagcc acaattaaga aatatataca     120
agaacaggaa aaacatgata tagcacttga taagttgagt gtaaagagt atgaagatcc     180 ctttagggat aatggcaagt agtacgaatg cctctttaag aggctagtga cgagtcaaaa    240
gcagtgaggc ttgaacaaag tgaaagccag cgtctttagg cgctggctgg tgatgtgggc    300 ttatagcccct tgttcaaacc acccgtttga cgggtggtca tgatttttt tgaatatttt    360 tcactatttt gttttacaaa ctagccacct tgtgttagac tatag                    405

<210> SEQ ID NO 26
<211> LENGTH: 410
<212> TYPE: DNA
<213> ORGANISM: Streptococcus suis
<220> FEATURE:
<223> OTHER INFORMATION: ivs 11

<400> SEQUENCE: 26
taccaccata tcaccaatat cacgcgccca gatgcgccaa tcgaagtggt ggatgtggct      60
ggttcccttt gtgaaaacaa cgacaagttt gcggtcaatc gtgaattacc acgggtagaa     120
gtaggagaca ccttggtcat tcatgacagt ggggcccacg gcttctccat gggctacaac    180
tacaacggtc gtctgcgttc ttctgaaatc cttttgcagg aagatggcac agcgcggatg    240
```

```
attcgtcgtg ctgaaacacc agaagactat ttcgcaacta tttacggttt tgattttgac    300
aggtaagtct tggaaaagac tagggaattt ggtataatag ggttattgaa agattgttaa    360
aaacaatcag aagtatactt tttagaagag tcaggagatt gacagatgaa               410
```

<210> SEQ ID NO 27
<211> LENGTH: 412
<212> TYPE: DNA
<213> ORGANISM: Streptococcus suis
<220> FEATURE:
<223> OTHER INFORMATION: ivs 15

<400> SEQUENCE: 27

```
gggctatggt ataattaaaa gacatgtata gtcagaatga aaatgaattg attgccattg     60
gtgagagaat tggaaaggcc tgtaagccaa atcaagttct agtattatca ggggatttgg    120
gtgctgggaa acaactctg accaagggtt tggccaaggg gttaaaaatt gaacagatga    180
ttaagagtcc tacttatacg attgttcgag agtatgaggg ggccatgccg ctctatcact    240
tagatgttta tcgaattgga gatgaccctg actcgattga tttggatgat tttctctatg    300
gaggaggtct aacggttatc gagtggggag aattactgga tgtcagtcta tttgatgact    360
atttgctcat tcgtatagag aaagagggag atggtcgacg attgacagtc ga            412
```

<210> SEQ ID NO 28
<211> LENGTH: 449
<212> TYPE: DNA
<213> ORGANISM: Streptococcus suis
<220> FEATURE:
<223> OTHER INFORMATION: ivs 16

<400> SEQUENCE: 28

```
gaaaattgtt gttgttttgg aacactagta gaccagaggc ttctagtaag gtagttgtgc     60
tcactgagga gggggaagga tgatggaagt tgagaaaagg agtaaggatt atgctcgtat    120
gtttgaccag caagtcggtc tttatgaaga ctatgctcgt ggacatggac tcaatgcaaa    180
atgtttatcc attctcatgt ggatttatta taatcccgga ggtgtgacgc aaaactgggt    240
cagtaagaag acctattcaa gcaaacaagt tgtcaatgct actgtaaaga attttttgga    300
tggaggcctg gtagttctag aggagaatcc agcagataag cgacataaga aaattaaatt    360
gacagaggag gggcaacaat tgctagtcg cattttggat cccttagagg aggcggaaaa    420
taaggcgctg tctcaactca gtcaggagg                                      449
```

<210> SEQ ID NO 29
<211> LENGTH: 410
<212> TYPE: DNA
<213> ORGANISM: Streptococcus suis
<220> FEATURE:
<223> OTHER INFORMATION: ivs 18

<400> SEQUENCE: 29

```
gcgttttgga acaagtacgt taagagaaac ctagagaaat ctagggtttt tgcttttata     60
tatctttaca ttgtttaaag aaaatagcat ttcaaaaact ttttgaaaaa aatgtgatat    120
tctgagcata tttttgaaa tcggtaacat ttatattgta aatatagtt cgtaaaaaaa    180 tatattttcg aaagtgagat tttacattat ggctaaaatc gttgttgtcg gtgctaacca    240
tgctggtact gccgcaatca aaactatgtt gacaaattat ggtcaagaaa atgaaatcgt    300
tgtatttgac caaaactcac atatttcatt cttgggttgt ggtatggctt tgtggatcgg    360
tgagcaaatt ggcggtcctg aaggactctt ctactcaaac aaagaagagt               410
```

<210> SEQ ID NO 30
<211> LENGTH: 437
<212> TYPE: DNA
<213> ORGANISM: Streptococcus suis
<220> FEATURE:
<223> OTHER INFORMATION: ivs 19
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t

<400> SEQUENCE: 30

```
tcgttccatt tgctggtgaa atgcccagca atacgcttcn tagcaataga agaaccaaat      60
agatggcact caatttcatg aggaagaaca gaagagtaaa aagcctgtct aaccacccta     120
acatagnata ttcctccttt tcatctatt ttatcaaaaa atcggtgctt ttctaccatt     180
tgtcaagttc atcaaggtat ttgacgaaaa atattttgtg tctcgtcatc caaataagga     240
aattgtttta ttttggacta agttacgtg taaaaagtgc atacaaaacc aacaccttat      300
gttgaaattt tttgataagg tgttacaatg atagagcata aacagttta ccgattttgg     360
gttgaagcgt aatcgtaaaa tttgttatgc ataatgaggt aatacattgt ccgaatgaga    420
cgatgtatgg aggcaat                                                    437
```

<210> SEQ ID NO 31
<211> LENGTH: 417
<212> TYPE: DNA
<213> ORGANISM: Streptococcus suis
<220> FEATURE:
<223> OTHER INFORMATION: ivs 2, 4, 28
<220> FEATURE:
<221> NAME/KEY: misc_feature
<222> LOCATION: (58)..(58)
<223> OTHER INFORMATION: n is a, c, g, or t

<400> SEQUENCE: 31

```
aagacggcgt caaggatgac aatcttgtgg tgacgaccac ccagaaactg gcgtagcntt     60
taccgtggcc ggaatcatga tcgcggtttt ccagccgttc atgcagttcg gttgttgctt   120
tgaacagcaa gaatatcccc ccgaacaaca taatcaggtc gcgtccggag aaggagaaat    180
ccatgacggt aaaatagcgg tttggtcagc gtgaccatcc atgaaatcag cgacagcagc   240
cccagacgca taatcagcgc cagtgataac cccagcaaac gcgctttatc gcgttgtttt    300
ggcggcagtt tgtcagcaag aatggcgatg aagaccaggt tatcgatacc cagcacaatt    360
tcgagaacaa caagcgtgag tagccccgcc caaattgagg ggtccattaa gaattcc       417
```

<210> SEQ ID NO 32
<211> LENGTH: 444
<212> TYPE: DNA
<213> ORGANISM: Streptococcus suis
<220> FEATURE:
<223> OTHER INFORMATION: ivs 20

<400> SEQUENCE: 32

```
agttcagatg ttcggtttag gaattgccgg cgtctggctg tcgattttga tggacctgct     60
cttgcgagcg attttctga cttggaggtt tattgtgcaa acacgaaaac tggctgaata   120
ggctagtttt ttggtataat atcagtagaa tgataaaaag gagataatca gatgaaaacc    180
attcacacag ataaggcacc tgcagcaatt ggcccatacg ttcaagggaa ggttgttgga    240
```

```
aatttcctat tgcctctgg tcaagttcct ttgtcacctg aaactggtga agtggttggt      300
gaaaccattc aggagcagac tgagcaagtc ttgaaaaata tcgcagcaat tttatcagaa      360
gcaggaacag actttgacca tgtggtgaag acgacttgtt tcctaaaaga tatgaatgat      420
tttgtagcct taatgaagt ttat                                              444

<210> SEQ ID NO 33
<211> LENGTH: 480
<212> TYPE: DNA
<213> ORGANISM: Streptococcus suis
<220> FEATURE:
<223> OTHER INFORMATION: ivs 23, 24

<400> SEQUENCE: 33
tctgcactgt tgcgctgcct ataagttcta cgttcagtag tagatgaaat gttcagagga       60
agtggtatgg gttccaactt agtaaaatta gtcattgatg atttggcgaa cagaaattcc      120
aaagcctttc aaatcgcagt tgaagaagag aaattgggaa cctggaagtt ctacaagaaa      180
ttagttttga agaacaggac gggctagtct atttgcgaaa acgcaagagt tcagcaaatt      240
cttgcttttt ttgatataat ggtagaagca gttttaagag gtatcaggta tgaatattca      300
acaattacgc tacgttgtag ccattgcaaa cagtggtaca tttcgagagg cggctgagaa      360
aatgtatgtg tcccagccta gtttgtccat ttccattcgt gatttggaaa aagagttagg      420
ttttcaaatt tttagccgaa ctagttcagg aactttttg acacaaaaag ggatggaatt      480

<210> SEQ ID NO 34
<211> LENGTH: 418
<212> TYPE: DNA
<213> ORGANISM: Streptococcus suis
<220> FEATURE:
<223> OTHER INFORMATION: ivs 25
<220> FEATURE:
<221> NAME/KEY: misc_feature
<222> LOCATION: (359)..(359)
<223> OTHER INFORMATION: n is a, c, g, or t

<400> SEQUENCE: 34
ggagatagca atgcttaata tttttgtatt agaagatgat ttttttcagc agagcaggtt       60
agaaaatgct attaggcagt gtgttgaaga acgtcagta aggtataaat tcctagaagt      120
ttttggtaaa ccaaatcaat tattggaatc aattgaggaa gcagggaatc atcaattttt      180 cttttttagat attgaaataa aaggagaaga aaagaaagga atggaaatcg ctaaagaaat      240
ccgggctcga gatccttatg ctgctattgt ctttgtaaca actcactcag aatttatgcc      300
agtaacatat cgttatcagg tttctgcttt agattttata gataaaggcc tggaggatng      360
tgactttcaa aaggcagtat cagatgtctt agtgcatgct tttgaaaata ttgatcat        418

<210> SEQ ID NO 35
<211> LENGTH: 446
<212> TYPE: DNA
<213> ORGANISM: Streptococcus suis
<220> FEATURE:
<223> OTHER INFORMATION: ivs 29

<400> SEQUENCE: 35
ggcaagggtg ggtaaatttc taattggtga caaggcactt gaattctacc cagatagcaa       60
cgttgaacgc tatatccaga ttccttggtc agaaatgact agcattggcg caaaacgttt      120
ctggcaaagc aatcagccgt catttgtgaaa tttatacaga gaaagtcga tttcttgttg      180 gcatctaaag attctggtaa gattcttaaa attgcccgtg agcatatcgg caatgaaaaa      240
```

```
gttgtgaaat taccgactct tatgcaaaca atcggcagaa aaatttcgaa tctatttgcc      300
aaaaaataaa aattcaagta taatagtaga aacggataag tagcatctgg ctccttccag      360
aaagtctgcg gtcgctgtga gcagatagga aaaagttgtg aaattctacc gttatgaaat      420
tatcaaaata caatcaagtg cacaga                                           446

<210> SEQ ID NO 36
<211> LENGTH: 416
<212> TYPE: DNA
<213> ORGANISM: Streptococcus suis
<220> FEATURE:
<223> OTHER INFORMATION: ivs 3

<400> SEQUENCE: 36
ggattatcta ctataagcag tattcagaag ggcatgagga caagaaatcc tacaagattc       60
tacaagaagt aggcatgagc cagaaggctg tcaagaaaac aattaactcc caaacactta      120
cggtcttctt tatgcctttg gtcatggcga ccctacactt tgtcatcgcc cttatcatgc      180
tcaagcaaat gctactaagt tttggtgtta cctcatcact aatgatttac acagtcagtg      240
gcatcaccct actggcagtc actctgattt actttgtcat ttacaagtgg actagtcgca      300
cttattatcg cattattgaa cggtagcaga agtctcgcct tgtgcgagat ttcttgcttt      360
ttcagggaaa tggtgttaca atggtaatac caaaggaata ctcgaagagg tgagaa         416

<210> SEQ ID NO 37
<211> LENGTH: 263
<212> TYPE: DNA
<213> ORGANISM: Streptococcus suis
<220> FEATURE:
<223> OTHER INFORMATION: ivs 31
<220> FEATURE:
<221> NAME/KEY: misc_feature
<222> LOCATION: (104)..(104)
<223> OTHER INFORMATION: n is a, c, g, or t

<400> SEQUENCE: 37
acgaaaatdg atggatccat gcataaactg catcccttaa cttgttttc gtgtgcctat        60 tttttgtgaa tcgaattcga gctcgcccct cctgaccacc tatntgcatc aagtgccaaa      120
tgaccagtcg agtgtgcggt tagacaacta ctatacgggc aaggaactgg agattgagtt      180
ggatgtggct ttgactccta gccaaaatgc ccagcggtac ttcaagaagt accagaaact      240
caaggaggcg gtcaagcacc tga                                              263

<210> SEQ ID NO 38
<211> LENGTH: 403
<212> TYPE: DNA
<213> ORGANISM: Streptococcus suis
<220> FEATURE:
<223> OTHER INFORMATION: ivs 32, 35

<400> SEQUENCE: 38
atatttgctc tcctgctctt taggggacaa tggaaaaagt agtctgtatc caacatttta       60
caaagtagga ttttttctat aaaatagatt gtatatgaca ttcaaatcca ttctcaaaca      120
actcaaacta tttgattata tcttaatcgg attcacccta gttttatcct ttcttccagc      180 aattttttacc tacacacaac tgacaacaga tgcaaatgag gcaaaacaa ttgcctatgt      240 ccgcatcaat ggtgaggtgg tcgaccaatt tgaattatca aaggacacac cccgtcaaga      300
aaagacctac tatcccaatg aagggcaata caatatcatt gaagttgatg gcgaacgcat      360
tcgtgtcaag gaagacaata gcccagacca aatcgccgtt atg                        403
```

<210> SEQ ID NO 39
<211> LENGTH: 401
<212> TYPE: DNA
<213> ORGANISM: Streptococcus suis
<220> FEATURE:
<223> OTHER INFORMATION: ivs 33

<400> SEQUENCE: 39

```
actcagttga acggagtagg atttataggt aaattgcctc caaatatcgt aagacaatcc      60
tctattgaaa aatagggat tgtttgttta gaataatgg tggagattct gtaaaaagcg      120
aaagtggttg gaaagttagg gtttagccga gaaaagaga cttttctatc tatctttcac      180
aattttctgt caatttgtgg tagaataaa aaaatagatt ttttatgagg gataccatga      240
cattagtata tcaatcaaca cgcgatgcta aaaatactgt atcggctagt caagcgattt      300
tgcagggctt ggcgaccgac ggtggtttgt ttacaccgct ttctattcca acagttgact      360
tggattttc tgttttgaaa gatgcttctt atcaagacgt t                          401
```

<210> SEQ ID NO 40
<211> LENGTH: 404
<212> TYPE: DNA
<213> ORGANISM: Streptococcus suis
<220> FEATURE:
<223> OTHER INFORMATION: ivs 34

<400> SEQUENCE: 40

```
gtttatcgtt cgctggagga aaagggctat aatccgatta accaaatcat tggctatgta      60
ttaagtgggg accctgctta tattcctcgc tataatgatg cccgcaatca gattcgtaag      120
catgaacgag atgaaatcat tgaagaattg gtgcgctact atttgaaagg gaatgggatt      180
gacctctaat gagaataatg ggattagacg tcggttccaa gacagttggt gtagccattt      240
cagatccgtt aggtttcacg gcccaagggt tggaaatcat cccaatcgat gaagaaaagg      300
gcgaattcgg tctggagcgt ttgaccgaac ttgtagaaca gtacaaggtt gataaatttg      360
ttgtaggctt gccgaagaat atgaataata ctagtggtcc acgt                       404
```

<210> SEQ ID NO 41
<211> LENGTH: 384
<212> TYPE: DNA
<213> ORGANISM: Streptococcus suis
<220> FEATURE:
<223> OTHER INFORMATION: ivs 36

<400> SEQUENCE: 41

```
ggtataatta tctgataaaa aactttggag acgacagtga gtttagaaaa ttacatgccg      60
gatttgcct tggaaaaggc ttatgacgtg accgtcgaaa gcttgaaaaa acatggcata      120
aaagtagtgt tgttgactt ggataatacc ttgattgctt ggaataatcc cgatggtacg      180
ccagagatgc gccagtggtt acatgatttg caggacgcag gtattcctgt tgtggtggtg      240
tctaacaata aatacgaacg tgtcaaacgg gcggttgaaa aatttgggat tgaatttgaa      300
gccttcgctc tcaagccttt cacctttggg attaaccgtg ctttgaaacg ctttgatgtc      360
cagccgtatg aggtaattat gatt                                            384
```

<210> SEQ ID NO 42
<211> LENGTH: 413
<212> TYPE: DNA
<213> ORGANISM: Streptococcus suis
<220> FEATURE:
<223> OTHER INFORMATION: ivs 5, 10, 12, 22

```
<400> SEQUENCE: 42
acgcacttgc tcgcgtagtc gatgaattag atgtacccgt tatggctttc ggtcttaaaa      60
atgatttccg aaatgaacta tttgaaggtt cccaacattt gctcttattg gctgataaat     120
tagatgaaat caaacaatc tgccaatatt gttctaaaaa agcgacaatg gttttgagaa      180
cacaggatgg aaaacctact tatgaaggag aacaaatcca aattggtggc aatgaaacct    240
acattcctgt ctgtcgcaaa cattattttt caccagaaat taaagattta ccctaatttt    300
tgaaaatgaa atgagaagca actgtaaact gagcaactat atagaactga atttgcctat    360
gactctgtgc caattttcat aacttacata ctacggcaaa ggaattgaac acg           413

<210> SEQ ID NO 43
<211> LENGTH: 428
<212> TYPE: DNA
<213> ORGANISM: Streptococcus suis
<220> FEATURE:
<223> OTHER INFORMATION: ivs 6, 7, 13, 14

<400> SEQUENCE: 43
gaagggatta acaatccta tgctattcag gctgttcgtg aaattcggat tatcgttcat      60
cctaacaagg tcactgatga tcagattacc atcttggccc atgatgttcg tgagaaaatt    120 gaaataatc tggattatcc aggaaatatc aaaatcacag ttatccgtga acaagagca      180 acagatgttg ctaagtaaat gtagaagagt ccgaagggct ctttttctac tggctcaaag   240
ttcgttttgg gttgggaata gaaaatagaa aatattttaa tcgtatttaa aagcagttga    300
aattcatgct aaattttgtt acactagaat gaaagattta aaggagata tcatgaaaga     360 gcgaggctta ctcattgtct tttctggtcc atctggtgcc ggaaaaggaa cagttcgaaa    420
ggaaattt                                                              428

<210> SEQ ID NO 44
<211> LENGTH: 383
<212> TYPE: DNA
<213> ORGANISM: Streptococcus suis
<220> FEATURE:
<223> OTHER INFORMATION: ivs 8

<400> SEQUENCE: 44
cttcaaagga ccccaggacc tttgaattct caaatacgca tcatgttgac agttgccaca      60
cctacaccaa aatcaaatgc caacaagcgt tgagtcgggt aatagcgtaa gtagcgcaag    120
gtcatgataa gctgctcttc catacttaga cggcgtgggc gtcctccttt tcggtgttgc    180
tcttgataag cgtcagtgag acaatcaagc atcagatgaa acgtcgcttt tttacaccta    240
tcaacaattt gaaattctct gagtttaatt ttaagacttt ttcgtatgtt gtttccatac    300
ctttagtata ccgcctttga gttaccgaac aagtctattg ctaaacttga tgaaggttgt    360
attgtctgtt ataatattgg ata                                             383

<210> SEQ ID NO 45
<211> LENGTH: 415
<212> TYPE: DNA
<213> ORGANISM: Streptococcus suis
<220> FEATURE:
<223> OTHER INFORMATION: ivs 9, 17

<400> SEQUENCE: 45
gcctatgaga ctcattttcc ctgtctcaac tgctctaagc aattgttaca ggttggttgt      60
aagcgggttg tctatatcaa tgaataccgc atggatgact atgctcagta cttgtataaa    120
```

-continued

```
gaaaagggct gtgagttggt tcatttgcct ctagaggtgg ttaaacaggc atttgcagat    180
gccgaattta tctaatgatt ttgtagaaga gtggttgcat agaacaaccc tctttatctt    240
taagaaaatg ctaggatagt cggtcaatct atgctatact agaaacgtta ttaagtcccg    300
aaaaggtagt ttatagacta gttaatattt gcagaaacac ttgaaacaca attaaagaaa    360
ctggtaatat tgaatagtaa gcgtaaaaac tttactacac ttcagtcact atttt         415

<210> SEQ ID NO 46
<211> LENGTH: 45
<212> TYPE: DNA
<213> ORGANISM: artificial sequence
<220> FEATURE:
<223> OTHER INFORMATION: PCR primer corresponding to positions 250 to
      273 of the fbps gene

<400> SEQUENCE: 46
gcggatccga tgacgatgac aaatcttttg acggattttt tttac                     45

<210> SEQ ID NO 47
<211> LENGTH: 32
<212> TYPE: DNA
<213> ORGANISM: artificial sequence
<220> FEATURE:
<223> OTHER INFORMATION: PCR primer corresponding to positions1911 to
      1892 of the fbps gene

<400> SEQUENCE: 47
cccaagcttg ggcatgaact agattttcat gg                                   32
```